US006703221B1

(12) United States Patent
Chan et al.

(10) Patent No.: US 6,703,221 B1
(45) Date of Patent: Mar. 9, 2004

(54) NOTCH RECEPTOR LIGANDS AND USES THEREOF

(75) Inventors: Vivien Chan, San Francisco, CA (US); Michael Rohan, San Francisco, CA (US); Lewis T. Williams, Mill Valley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/641,612

(22) Filed: Aug. 17, 2000

Related U.S. Application Data

(60) Provisional application No. 60/149,934, filed on Aug. 19, 1999.

(51) Int. Cl.[7] ................................................ C12P 21/02
(52) U.S. Cl. .................... 435/69.1; 536/23.5; 530/350; 435/320.1; 435/252.3; 435/325
(58) Field of Search ........................ 530/350; 536/23.5; 435/320.1, 252.3, 325, 69.1

(56) References Cited

U.S. PATENT DOCUMENTS

| | | | |
|---|---|---|---|
| 4,959,314 A | 9/1990 | Mark et al. | ................. 435/69.1 |
| 5,648,464 A | 7/1997 | Artavanis-Tsakonas et al. | . 530/350 |
| 5,869,037 A | 2/1999 | Crystal et al. | ............. 424/93.2 |

FOREIGN PATENT DOCUMENTS

| | | |
|---|---|---|
| WO | WO 98/45434 | 10/1998 |
| WO | WO 98/51799 | 11/1998 |

OTHER PUBLICATIONS

Boulter et al., DatabaseGenEmbl, Accession No., AF084576, Aug. 30, 1998 (see attached sequence alignment).*
Database EST, Accession No., AI089793, Oct. 1, 1998 (see attached sequence alignment).*
Dunwoodie et al., "Mouse Dll3: a Novel Divergent Delta Gene Which May Complement the Function of Other Delta Homologues During Early Pattern Formation in the Mouse Embryo," *Development* 124(16):3065–3076, Aug. 1997.
Ellisen et al., "TAN–1, the Human Homolog of the Drosophila Notch Gene, is Broken by Chromosomal Translocations in T Lymphoblastic Neoplasms," *Cell* 66(4):649–661, Aug. 23, 1991.
Fitzgerald et al., "Interchangeability of Caernorhabditis Elegans DSL Proteins and Intrinsic Signalling Activity of Their Extracellular Domains in Vivo,"0 *Development* 121(12):4275–4282, Dec. 1995.
Gray et al., "Human Ligands of the Notch Receptor," *Am J Pathol.* 154(3):785–794, Mar. 1999.
Joutel et al., "Strong Clustering and Stereotyped Nature of Notch3 Mutations in CADASIL Patients," *Lancet* 350(9090):1511–1515, Nov. 22, 1997.

Lendahl, "A Growing Family of Notch Ligands," *BioEssays* 20(2):103–107, Feb. 1998.
Li et al., "Alagille Syndrome is Caused by Mutations in Human Jagged1, Which Encodes a Ligand for Notch1," *Nature Genetics* 16(3):243–251, Jul. 1997.
Magovern et al., "Regional Angiogenesis Induced in Nonischemic Tissue by an Adenoviral Vector Expressing Vascular Endothelial Growth Factor," *Human Gene Therapy* 8:215–227, Jan. 20, 1997.
Montesano et al., "Tumor–Promoting Phorbol Esters Induce Angiogenesis in Vitro," *Cell* 42(2):469–477, Sep. 1985.
Oda et al., "Mutations in the Human Jagged1 Gene are Responsible for Alagille Syndrome," *Nature Genetics* 16(3):235–242, Jul. 1997.
Radtke et al., "Deficient T Cell Fate Specification in Mice With an Induced Inactivation of Notch1," *Immunity* 10(5):547–558, May 1999.
Salloway et al, "CADASIL Syndrome: a Genetic Form of Vascular Dementia," *J. Geriatr. Psychiatry Neurol.* 11(2):71–77, Summer 1998.
Shirayoshi, "Proto–Oncogene of INT–3, a Mouse Notch Homologue, is Expressed in Endothelial Cells during Early Embryogenesis," *Genes to Cells* 2(3):213–224, Mar. 1997.
Uyttendaele, "Notch4/int–3, a Mammary Proto–Oncogene, is an Endothelial Cell–Specific Mammalian Notch Gene," *Development* 122(7):2251–2259, Jul. 1996.
Xue et al., "Embryonic Lethality and Vascular Defects in Mice Lacking the Notch Ligand Jagged1," *Hum. Mol. Gen.* 8(5):723–730, May 1999.
Zecchini et al., "An Activity of Notch Regulates JNK Signalling and Affects Dorsal Closure in Drosophila," *Current Biology* 9(9):460–469, Apr. 21, 1999.
Zimrin et al., "An Antisense Oligonucleotide to the Notch Ligand Jagged Enhances Fibroblast Growth Factor–Induced Angiogenesis in Vitro," *Jour. Biol. Chem.* 271(51):32499–32502, Dec. 20, 1996.
Abstract of JP11299493, esp@cenet database, Nov. 2, 1999.
Genbank Accession No. AB013440, Oct. 9, 1998.
Genbank Accession No. AL078605, Apr. 29, 2000.
Genbank Accession No. Z48825, Mar. 30, 1995.
Geneseq_d database, Accession No. X16303, Apr. 22, 1999.
Derwent dgene database, Accession No. AAX16303, Apr. 22, 1999.

* cited by examiner

*Primary Examiner*—Lorraine Spector
*Assistant Examiner*—Eileen B. O'Hara
(74) *Attorney, Agent, or Firm*—Jane E. R. Potter; Charlene A. Launer; Robert P. Blackburn

(57) ABSTRACT

The invention provides polynucleotides encoding Notch receptor ligands, encoded polypeptides, and antibodies specific to the polypeptides. Also provided are methods and compositions for enhancing or inhibiting angiogenesis as well as modulating immune responses.

9 Claims, 12 Drawing Sheets

FIG. 1A

```
3dm3p      VDQACAPGYMG ARCEFPM.... ......... HPDGASALPA APPGLRPCDP QRYLLPPALQ LLMAAGVAGA ALLLMHVRRR GHSQDAGSRL LAGTEPSVH ALPDAL NVL ....... 543
moused113p VDQACAPGYMG VRCEFAN.... ......... RPDGADAVPA APRGLRQADP QRFLLPPALQ LLMAAGLAGA ALLVIHVRRR GPGQDTGTRL LSGTEPSVH TLPDAL NVL ....... 553
hdelta1p   VDECARGYGG PNGGFLLPEL PPGPAWDLT EKLEGQGGPF PWVAVCAGVI ELMLMLLGC WAMMQVRLR LQKHR..... .....PADPCR GETETMNNLA NCQRE         599
w80813     vgngpygIF vg srcefpM. sr.ce.p    .gl.p      .gl.p      .....pbs    ......... qlr lr.... ......ngddgsr ...egmnls dfqkd 577

3dm3p                                                      RTQEGS GQGPSSSMDW NRPEDMDPQG IYVISRPSIY AREA......                        583
moused113p                                                RLQDGA GQGPSSSADW NHPEDQDSRS IYVIPAPSIY AREA......                        593
hdelta1p   KDISVSIIGA TQIIKNTNKKA DFHQDHSADK .NGFKARYPA VDYNLVQDLK GDTAVRDAH SKRDTKCQPQ GSSGEEKGTP TTLRGGEASE RKRPDSGCST SKDTK  703
w80813     n........ lipa aglknignqkk elevdcglidk sncgkqqnht ldynIcgpI grgt..... ......mpgktphs dkslgeko.p Ir lhsekpec r ... isomes prdsm 665

3dm3p                                           583
moused113p                                      593
hdelta1p   YQSYVISEE KDECVIATEV                 723
w80813     yqsvcl isee rnecviatev               685
```

3md3 NUCLEOTIDE SEQUENCE: 1752 (SEQ ID NO:1)

```
ATGGTCTCCCCACGGATGTCCGGGCTCCTCTCCCAGACTGTGATCCTAGC
GCTCATTTTCCTCCCCCAGACACGGCCCGCTGGCGTCTTCGAGCTGCAGA
TCCACTCTTTCGGGCCGGGTCCAGGCCCTGGGCCCCGCGGTCCCCCTGC
AGCGCCCGGCTCCCCTGCCGCCTCTTCTTCAGAGTCTGCCTGAAGCCTGG
GCTCTCAGAGGAGGCCGCCGAGTCCCCGTGCGCCCTGGGCGCGGCGCTGA
GTGCGCGCGGACCGGTCTACACCGAGCAGCCCGGAGCGCCCGCGCCTGAT
CTCCCACTGCCCGACGGCCTCTTGCAGGTGCCCTTCCGGGACGCCTGGCC
TGGCACCTTCTCTTTCATCATCGAAACCTGGAGAGAGGAGTTAGGAGACC
AGATTGGAGGGCCCGCCTGGAGCCTGCTGGCGCGCGTGGCTGGCAGGCGG
CGCTTGGCAGCCGGAGGCCCGTGGGCCCGGGACATTCAGCGCGCAGGCGC
CTGGGAGCTGCGCTGCTCGTACCGCGCGCGCTGCGAGCCGCCTGCGGTCG
GGACCGCGTGCACGCGCCTCTGCCGTCCGCGCAGCGCCCCCTCGCGGTGC
GGTCCGGGACTGCGCCCCTGCGCACCGCTCGAGGACGAATCGGTGTGCCG
AGCAGGCTGCAGCCCTGAGCATGGCTTCTGTGAACAGCCCGGTGAATGCC
GATGCCTAGAGGGCTGGACTGGACCCCTCTGCACGGTCCCTGTCTCCACC
AGCAGCTGCCTCAGCCCCAGGGGCCCGTCCTCTGCTACCACCGGATGCCT
TGTCCCTGGGCCTGGGCCCTGTGACGGGAACCCGTGTGCCAATGGAGGCA
GCTGTAGTGAGACACCCAGGTCCTTTGAATGCACCTGCCCGCGTGGGTTC
TACGGGCTGCGGTGTGAGGTGAGCGGGGTGACATGTGCAGATGGACCCTG
CTTCAACGGCGGCTTGTGTGTCGGGGGTGCAGACCCTGACTCTGCCTACA
TCTGCCACTGCCCACCTGGTTTCCAAGGCTCCAACTGTGAGAAGAGGGTG
GACCGGTGCAGCCTGCAGCCATGCCGCAATGGCGGACTCTGCCTGGACCT
GGGCCACGCCCTGCGCTGCCGCTGCCGCGCCGGCTTCGCGGGTCCTCGCT
GCGAGCACGACCTGGACGACTGCGCGGGCCGCGCCTGCGCTAACGGCGGC
ACGTGTGTGGAGGGCGGCGGCGCGCACCGCTGCTCCTGCGCGCTGGGCTT
CGGCGGCCGCGACTGCCGCGAGCGCGCGGACCCGTGCGCCGCGCGCCCCT
GTGCTCACGGCGGCCGCTGCTACGCCCACTTCTCCGGCCTCGTCTGCGCT
TGCGCTCCCGGCTACATGGGAGCGCGGTGTGAGTTCCCAGTGCACCCCGA
CGGCGCAAGCGCCTTGCCCGCGGCCCCGCCGGGCCTCAGGCCCGGGGACC
CTCAGCGCTACCTTTTGCCTCCGGCTCTGGGACTGCTCGTGGCCGCGGGC
GTGGCCGGCGCTGCGCTCTTGCTGGTCCACGTGCGCCGCCGTGGCCACTC
CCAGGATGCTGGGTCTCGCTTGCTGGCTGGGACCCCGGAGCCGTCAGTCC
ACGCACTCCCGGATGCACTCAACAACCTAAGGACGCAGGAGGGTTCCGGG
GATGGTCCGAGCTCGTCCGTAGATTGGAATCGCCCTGAAGATGTAGACCC
TCAAGGGATTTATGTCATATCTGCTCCTTCCATCTACGCTCGGGAGGCCT
GA
```

FIG.5A

3md3 PROTEIN SEQUENCE: 583 (SEQ ID NO:2)

```
MVSPRMSGLLSQTVILALIFLPQTRPAGVFELQIHSFGPGPGPGAPRSPC
SARLPCRLFFRVCLKPGLSEEAAESPCALGAALSARGPVYTEQPGAPAPD
LPLPDGLLQVPFRDAWPGTFSFIIETWREELGDQIGGPAWSLLARVAGRR
RLAAGGPWARDIQRAGAWELRCSYRARCEPPAVGTACTRLCRPRSAPSRC
GPGLRPCAPLEDESVCRAGCSPEHGFCEQPGECRCLEGWTGPLCTVPVST
SSCLSPRGPSSATTGCLVPGPGPCDGNPCANGGSCSETPRSFECTCPRGF
YGLRCEVSGVTCADGPCFNGGLCVGGADPDSAYICHCPPGFQGSNCEKRV
DRCSLQPCRNGGLCLDLGHALRCRCRAGFAGPRCEHDLDDCAGRACANGG
TCVEGGGAHRCSCALGFGGRDCRERADPCAARPCAHGGRCYAHFSGLVCA
CAPGYMGARCEFPVHPDGASALPAAPPGLRPGDPQRYLLPPALGLLVAAG
VAGAALLLVHVRRRGHSQDAGSRLLAGTPEPSVHALPDALNNLRTQEGSG
DGPSSSVDWNRPEDVDPQGIYVISAPSIYAREA
```

FIG.5B

2hd1 NUCLEOTIDE SEQUENCE: 1307 (SEQ ID NO:3)

AGTACTCCTACCGCTTCGTGTGTGACGAACACTACTACGGAGAGGGCTGCTCCGTTTTCT
GCCGTCCCCGGGACGATGCCTTCGGCCACTTCACCTGTGGGGAGCGTGGGGAGAAAGTGT
GCAACCCTGGCTGGAAAGGGCCCTACTGCACAGAGCGTGAGTCTCTGGGAAGGCACCGCT
GGCTCACTCGTCCACGAACACGGACCACGCGCAGGGACGGGGCTTCCTGAGCCACGGGGG
GCTTGGGACTGTAGAGATGTTCTGGTGGGGAAACTGAGGCCCAGAGGACAGAAGTGGATT
GCTATAAGTCACAGCTCGTCAGTGGGGGGGTTGGGGTCAACGCAGACATTTTAACATCCC
AGGCTGTGTTTATCCACTATCGGAACTGCCTTTCTTAATCAGGGAGGATTTTAGAGACAG
GGCCAGGGGTCAGGAAGTAAAGCCAGTGCTACCCCCAGGGTGTGTGTATTAGAGAGGGAG
AGGAGGAAGGAAGGGAGGAACACAGAGAGAGCTTGTGTGTCAGGGGCACCATTTCAACCC
GAGTTCCCAGTGCTGGAACAGCATCACACTGGGAAACGTTCCATTTTCTCTCTGGAGCTG
GTGTGCTTGACCTCTCTGGAGCAAACGCCTTTCCGGATACTCCCTGTGACACGCACTGTC
TATGCTGGCCAGAGAGCAGGCTTTCACTCCTGTGGGCTGCTGAGGCCAGGTCTCCAAGGC
CTGTGTGGGCGAGGGGTGCACAGCCCCGTCTGGCTTGAATGCTCAGGCAGCACCTTGTCT
GGAAAAGCAATGTCTTCCCAATAGTGACAGAGGCTCTACCTGCCTCTTATTAGGTATTGA
TGTGTCAATGTCATGGCAGGCAGGTGACTAGGGCAGGGTTGGGGCCGTGCTGGCTCCTGG
TTCTGGCTCATGGGGACCTCAGGAGCCCTCTCTCCAGCTGACTGAGGCCTCGCCTGCACG
CCTGGCCGTCCCAGCCCATTGGTACCGGATTTCTCTACAGCTGGGGATTGGGTAGGTCCT
GGAGCTGCCCAGAAACTCCAGGGAACTGTCATTCTCCTTCCTTGGAACTGGACAACCTTG
GAGAGGGGCTCTGGGAGGCCCAGAACCTCTGGCAGGAGCTGGGTAGTGCCTGGGGTTGAG
GGTGGGTCTTCCCATTCACTGAGTGCCTTGATGTCCTTGCTCCTTAGCTTCCCAAATTCC
CTCCGGAACTTACTGAGCTCCTTCTAAGCTTTGCCTTGGCCTGAACTGGTTCTGGGGAAA
AAAAAAAAAAAAAAAAAAAAAAAAAAAAAAAAAAAAAAAAAAAAAAAA

2hd1 PROTEIN SEQUENCE: 81 (SEQ ID NO:4)

GRTDLKYSYRFVCDEHYYGEGCSVFCRPRDDAFGHFTCGERGEKVCNPGWKGPYCTERES
LGRHRWLTRPRTRTTRRDGAS

FIG.6

NOTCH RECEPTOR LIGANDS AND USES THEREOF

CROSS REFERENCE TO RELATED APPLICATION

This application claims a priority benefit of provisional application Serial No. 60/149,934 filed Aug. 19, 1999.

FIELD OF THE INVENTION

The present invention relates to receptors and ligands consisting of human Notch gene products, and uses of these receptors, ligands and derivatives thereof to modulate cell-cell interaction in biological processes and conditions including angiogenesis and cancer.

BACKGROUND OF THE INVENTION

The Notch pathway is involved in cell fate determination and differentiation, and signaling through the Notch pathway receptors is an evolutionarily conserved mechanism for cell-cell interaction. Notch proteins, of which four have been identified in humans (Notch 1, Notch 2, Notch 3 and Notch 4), are a family of closely related transmembrane receptors. Notch 4 is expressed specifically in endothelial cells (Shiratoshi, Y., *Genes Cells* 2:213–224, 1997; Uyttendaele, H., *Development* 122:2251–2259, 1996) and may play an important role in angiogenesis. When Notch is activated by a ligand, its intracellular domain is proteolytically cleaved and transported to the nucleus, along with CSL (CBF-1/Su (H)/Lag-1/RBP-J$_K$) transcription factor to activate transcription of downstream effectors. The resulting effector can repress the transcriptional activity of other genes encoding transcription factors for entry into terminal differentiation. The ligands that interact with the extracellular portion of Notch include Delta, Serrate, and Jagged; the ligands also are transmembrane proteins.

Adjacent cells of identical lineage can follow separate pathways of differentiation as a result of the Notch pathway. Sample pathways of differentiation include axis formation, cartilage formation, and somite formation. Through a process of lateral inhibition, one cell can suppress the neighboring cells from following the same path of differentiation. In one model, a Notch receptor is expressed on the cell surface of a "suppressed" cell, and interacts with a Notch ligand located on the cell surface of a dominating cell. After ligand interaction with a Notch receptor, the intracellular domain of the Notch receptor is cleaved and transported to the nucleus, where it forms a complex and affects gene transcription. (Lendahl, U., *BioEssays* 20:103–107, 1998.)

The ligand itself plays an important role in determining the fate of cells in the vicinity of Notch-expressing cells. In Drosophila, ligands including Delta and Serrate have been identified and studied. The corresponding genes in mammals include Dll-1 (Delta-1) and Dll-3 (Delta-3), as well as Jag-1 and Jag-2. Mutations and decreased expression of Delta are related to phenotypic changes, and a translocation in the human Notch 1 locus (TAN-1) has been found in T-cell acute lymphoblastic leukemia/lymphoma (Ellisen et al., *Cell* 66:649–661, 1991).

Mutations in the human Jagged 1 gene are associated with Alagille syndrome, which involves abnormal development of liver, heart, skeleton, eye, and face. Alagille patients also exhibit valvular and arterial stenonis and high incidence of intracranial hemorrhage. Four separate mutations, all frameshifts, have been identified in patients with the syndrome. (Li, L. et al., *Nature Genetics* 16:243–251, 1997; Oda, T. et al., *Nature Genetics* 16:235–242, 1997.) The mutations are likely to interfere with the ability of Jagged 1 to interact with Notch, thereby affecting the differentiation of cells whose fate would otherwise be determined by interaction of Notch with functional Jagged 1. Mice rendered genetically deficient for Jagged 1 exhibit defects in vascular development (Xue et al., *Hum. Mol. Gen.* 8:723, 1999). These results are consistent with the hypothesis that Jagged 1 is also involved in vascular development and integrity.

Mutations in Notch 3 are related to a syndrome known as CADASIL, for cerebral autosomal arteriopathy with subcortical infarction and leukoencephalopathy. (Jontel, A. et al., *Lancet* 350:1511–1515, 1997.) Missense mutations in the extracellular domain were found in 45 out of 50 CADASIL patients in one reported study. (Salloway, S. et al, *J. Geriatr. Psychiatry Neurol.* 11:71–77, 1998.) CADASIL patients exhibit recurrent ischemic stroke and severe vascular smooth muscle cell defect. Thus, mutations in the Notch gene itself can affect vascular integrity in adults.

In view of the importance of this signaling pathway and its role in human cell differentiation and disease, there is a need in the art for identification of genes involved in the pathway, and for methods and therapeutic agents for intervening in diseases and conditions related to defects in the Notch pathway.

SUMMARY OF THE INVENTION

The present invention relates to nucleotide sequences of human Notch ligand genes, and amino acid sequences of the encoded proteins, as well as derivatives and fragments thereof wherein the derivatives and fragments exhibit biological activity such as binding to Notch receptors.

The invention also relates to methods of modulating angiogenesis by using the Notch ligands of the invention, and derivatives and fragments thereof.

The invention further relates to modulation of endothelial cell proliferation using polynucleotides encoding all of part of the Notch ligands of the invention, such as antisense oligonucleotides that can target nucleic acid encoding the Notch ligand.

The invention still further relates to methods of modulating the development and maturation of T-cells and other cells of the immune system, thereby regulating cell-mediated immunity and antibody responses to alleviate conditions such as rheumatoid arthritis.

Notch ligands of the invention include those encoded by the 3md3 gene and the 2hd1 gene.

The invention relates to an isolated nucleic acid molecule comprising a polynucleotide selected from the group consisting of:

(a) a polynucleotide encoding amino acids from about 1 to about 583 of SEQ ID NO:2;

(b) a polynucleotide encoding amino acids from about 2 to about 583 of SEQ ID NO:2;

(c) a polynucleotide encoding amino acids from about 1 to about 81 of SEQ ID NO:4;

(d) a polynucleotide encoding amino acids from about 2 to about 81 of SEQ ID NO:4;

(e) the polynucleotide complement of the polynucleotide of (a)–(d); and (f) a polynucleotide at least 90% identical to the polynucleotide of (a)–(e).

The invention also relates to an isolated nucleic acid molecule consisting of a nucleic acid comprising 50–1752 contiguous nucleotides from the coding region of SEQ ID NO:1.

The invention further relates to an isolated nucleic acid molecule comprising a polynucleotide encoding a polypeptide wherein, except for at least one conservative amino acid substitution, said polypeptide has an amino acid sequence selected from the group consisting of:

(a) amino acids from about 1 to about 583 of SEQ ID NO:2;

(b) amino acids from about 2 to about 583 of SEQ ID NO:2;

(c) amino acids from about 1 to about 81 of SEQ ID NO:4; and (d) amino acids from about 2 to about 81 of SEQ ID NO:4.

The invention still further relates to an isolated polypeptide comprising amino acids at least 95% identical to amino acids selected from the group consisting of:

(a) amino acids from about 1 to about 583 of SEQ ID NO:2;

(b) amino acids from about 2 to about 583 of SEQ ID NO:2;

(c) amino acids from about 1 to about 81 of SEQ ID NO:4; and (d) amino acids from about 2 to about 81 of SEQ ID NO:4.

The invention also relates to a complex comprising a protein comprising an amino acid sequence selected from the group consisting of SEQ ID NO:2 and SEQ ID NO:4.

The invention further relates to a complex comprising a fragment of the amino acid sequence selected from the group consisting of SEQ ID NO:2, SEQ ID NO:4, and a Dishevelled protein wherein said fragment is capable of forming a complex with said Dishevelled protein.

BRIEF DESCRIPTION OF THE DRAWINGS

Figure 1A:
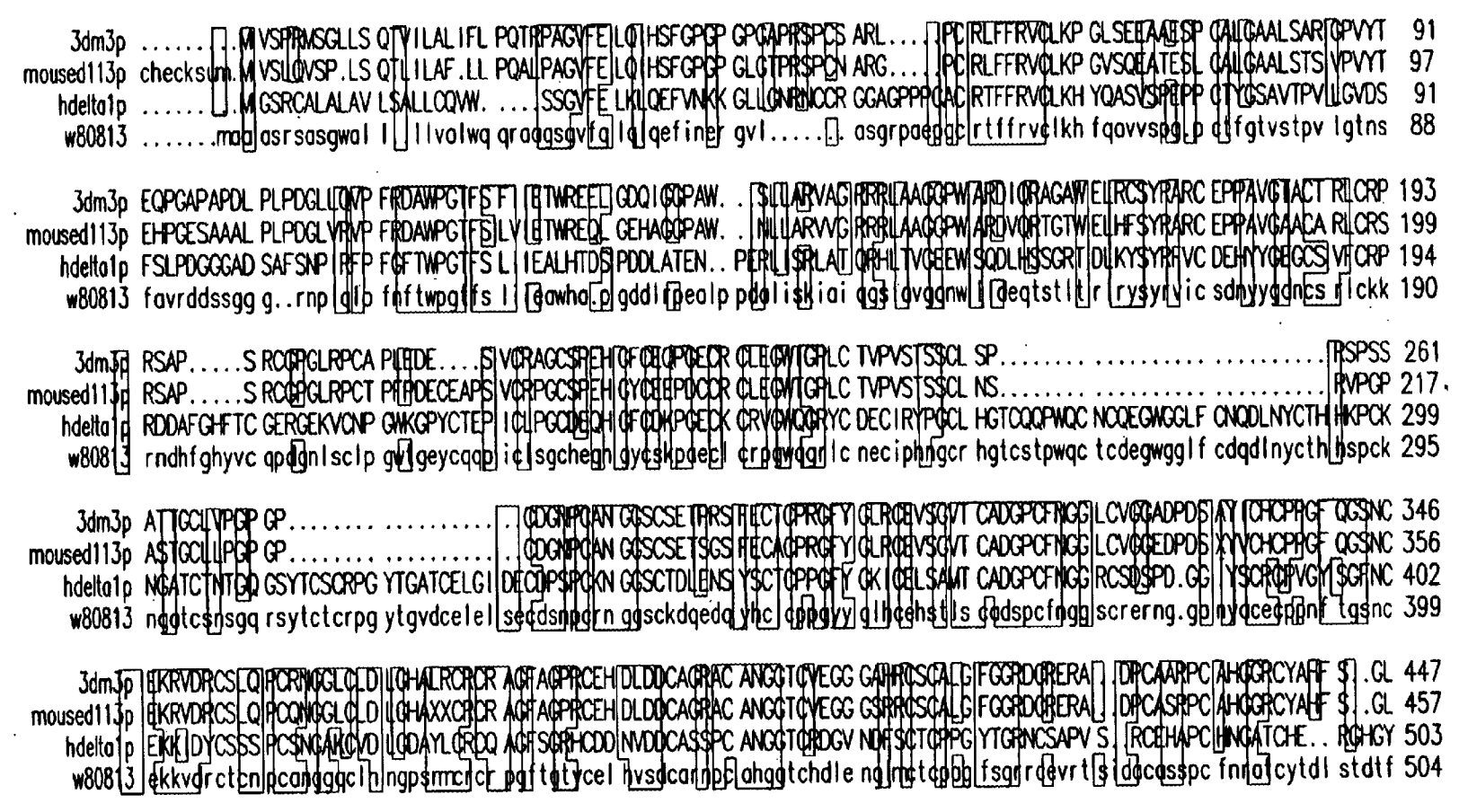

FIG. 1 is an alignment of the amino acid sequences of novel human Notch ligand, 3md3 (SEQ ID NO:2), of the present invention (SEQ ID NO:1), the mouse ortholog Delta-3 (3721842_md3; SEQ ID NO:5), a human Delta polypeptide (w80813_hd3; SEQ ID NO:6), and human sequence hdelta1p (SEQ ID NO:7).

Figure 3A:
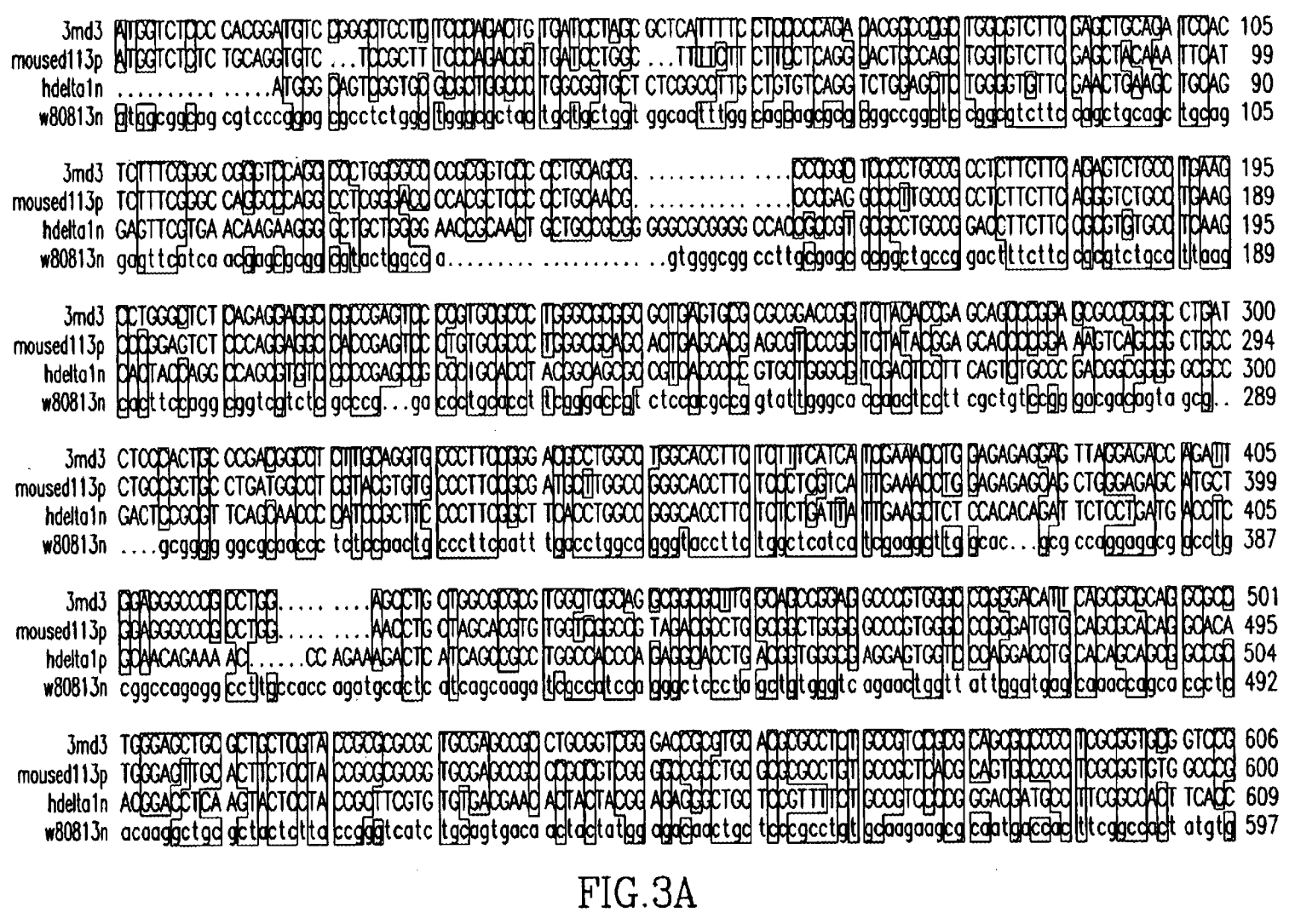
Figure 3B:
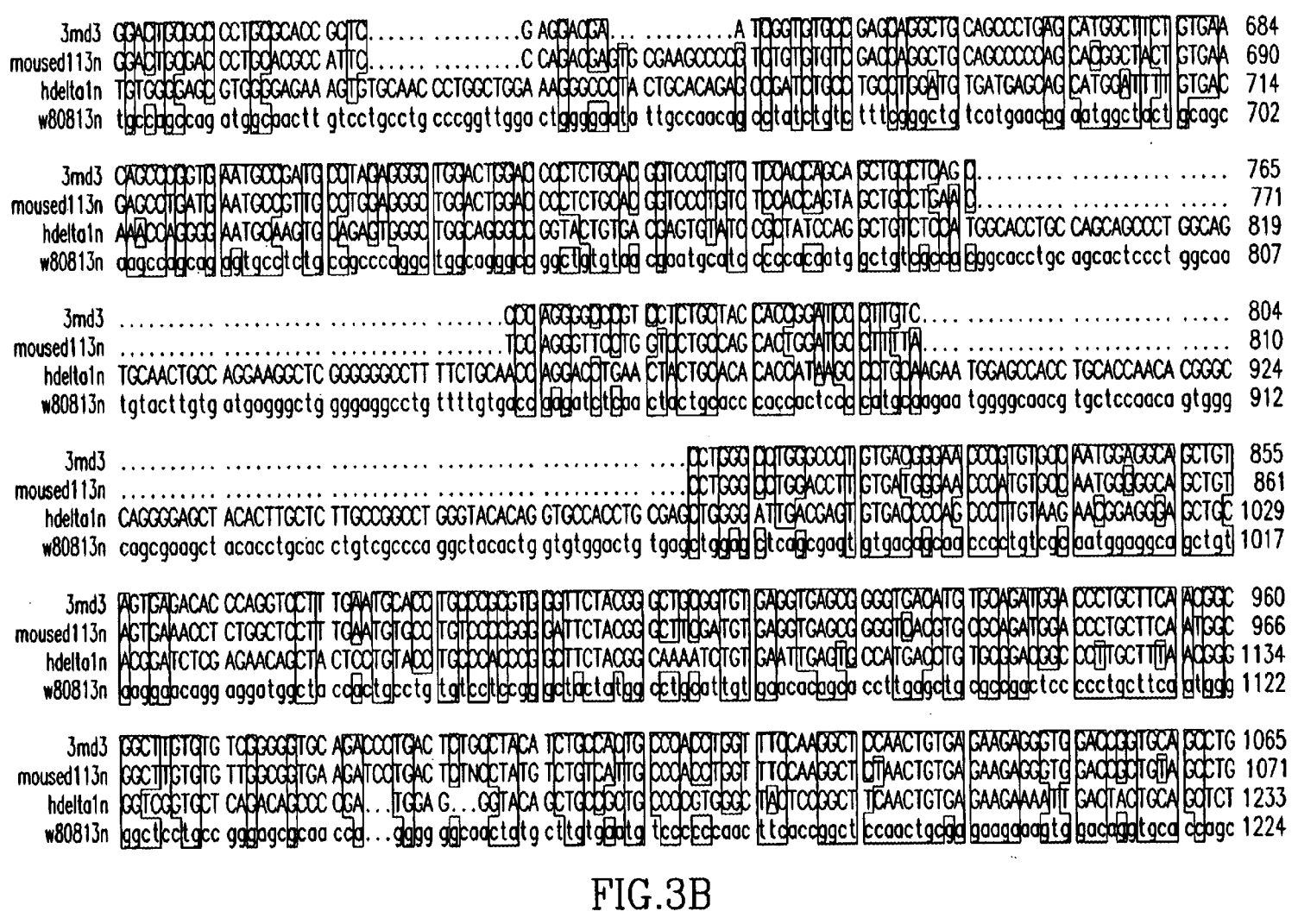
Figure 3D:
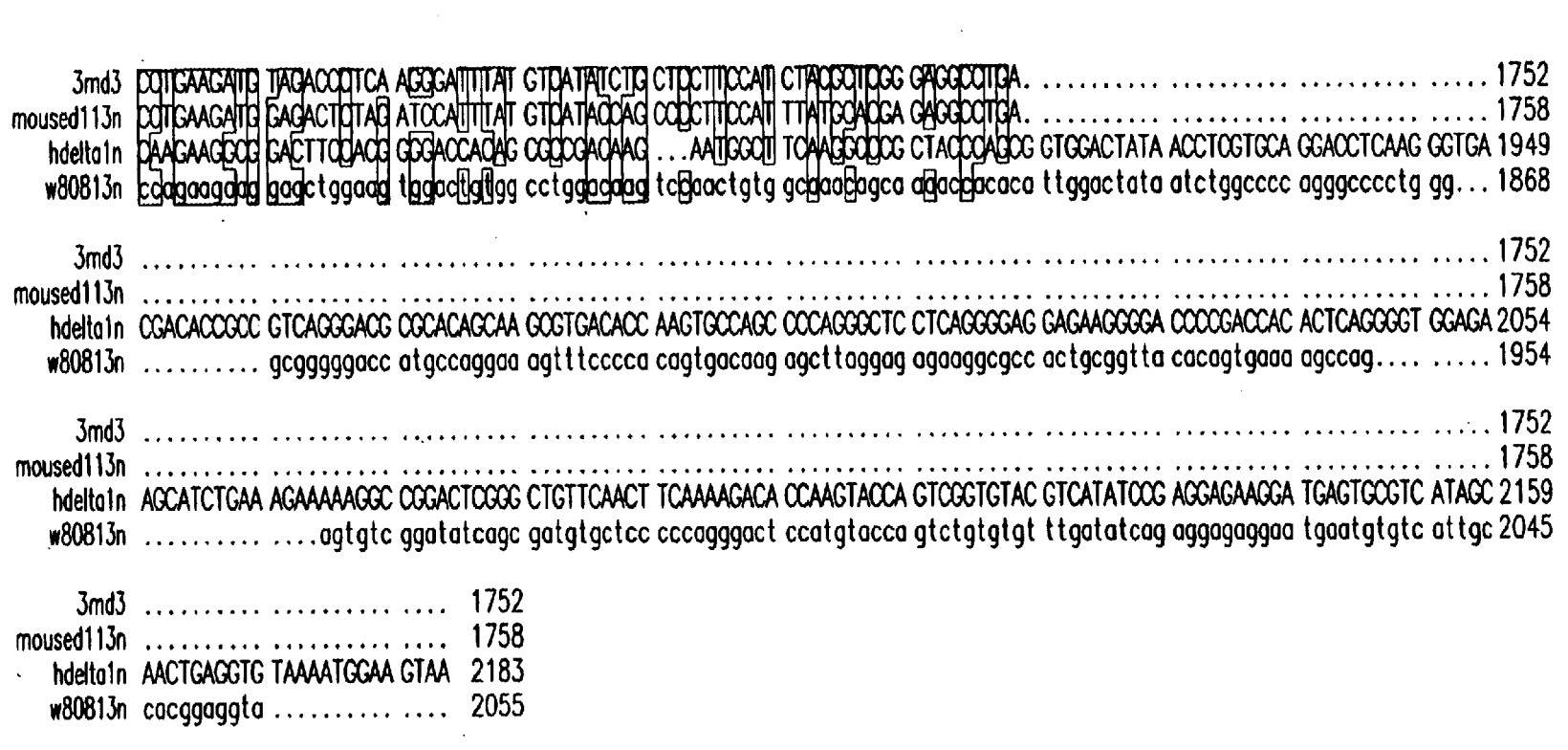

FIG. 3, FIG. 3A–FIG. 3D is an alignment of the nucleotide sequences of 3md3 (SEQ ID NO: 2), mouse dll3, hdelta, and W80813.

FIGS. 5A and B provide the polynucleotide (SEQ ID NO:1) and amino acid (SEQ ID NO:2) sequences of 3md3.

FIG. 6 provides the polynucleotide (SEQ ID NO:3) and amino acid (SEQ ID NO:4) sequences for 2hd1.

DETAILED DESCRIPTION OF THE INVENTION

Introduction

Figure 2:
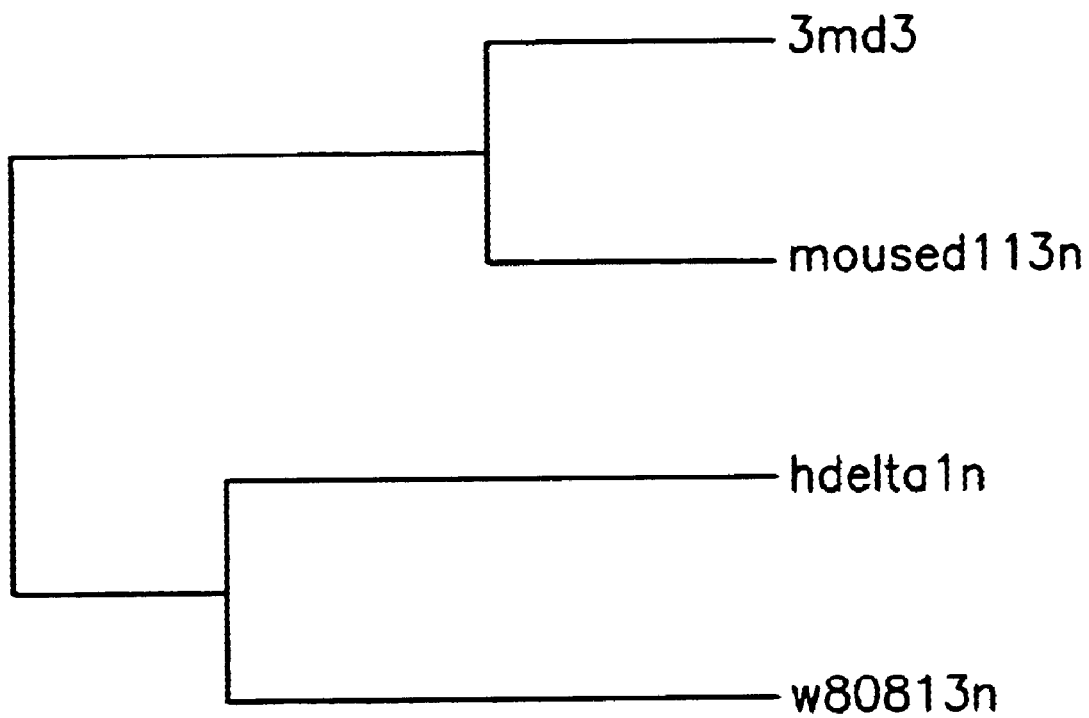
FIG. 2 is a protein phylogenic analysis based on the sequences of FIG. 1, and shows that 3md3 is more closely related to murine Delta 3 than is the human sequence W80813_hd3 or human sequence hdelta1p.
Figure 4:
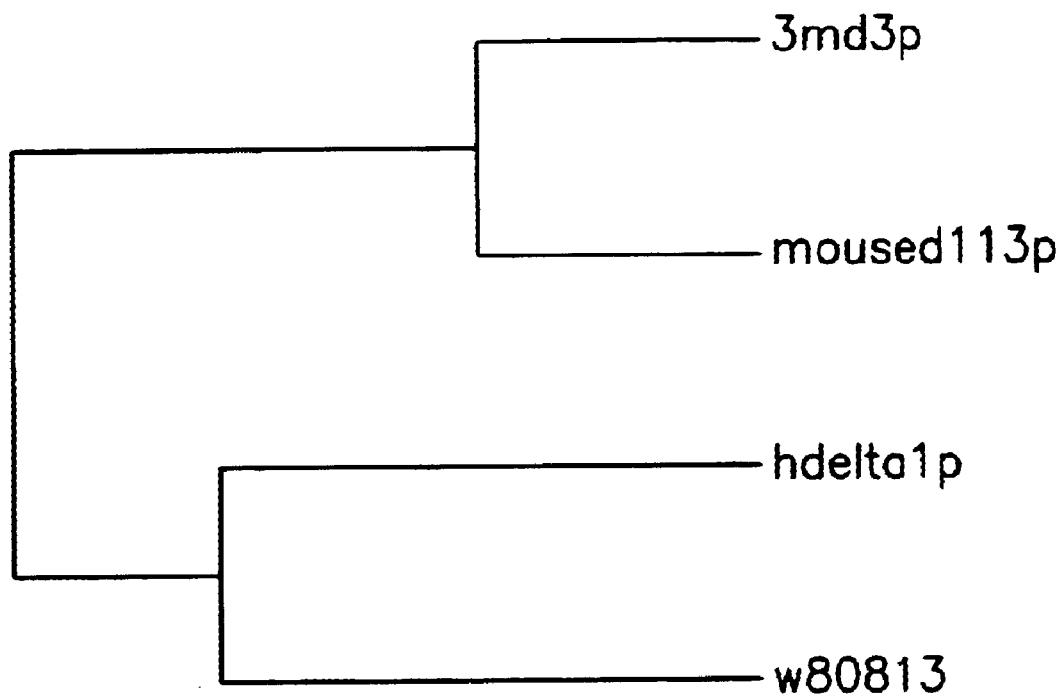
FIG. 4 is a polynucleotide phylogenic analysis based on the sequences of FIG. 3.
Figure 7:
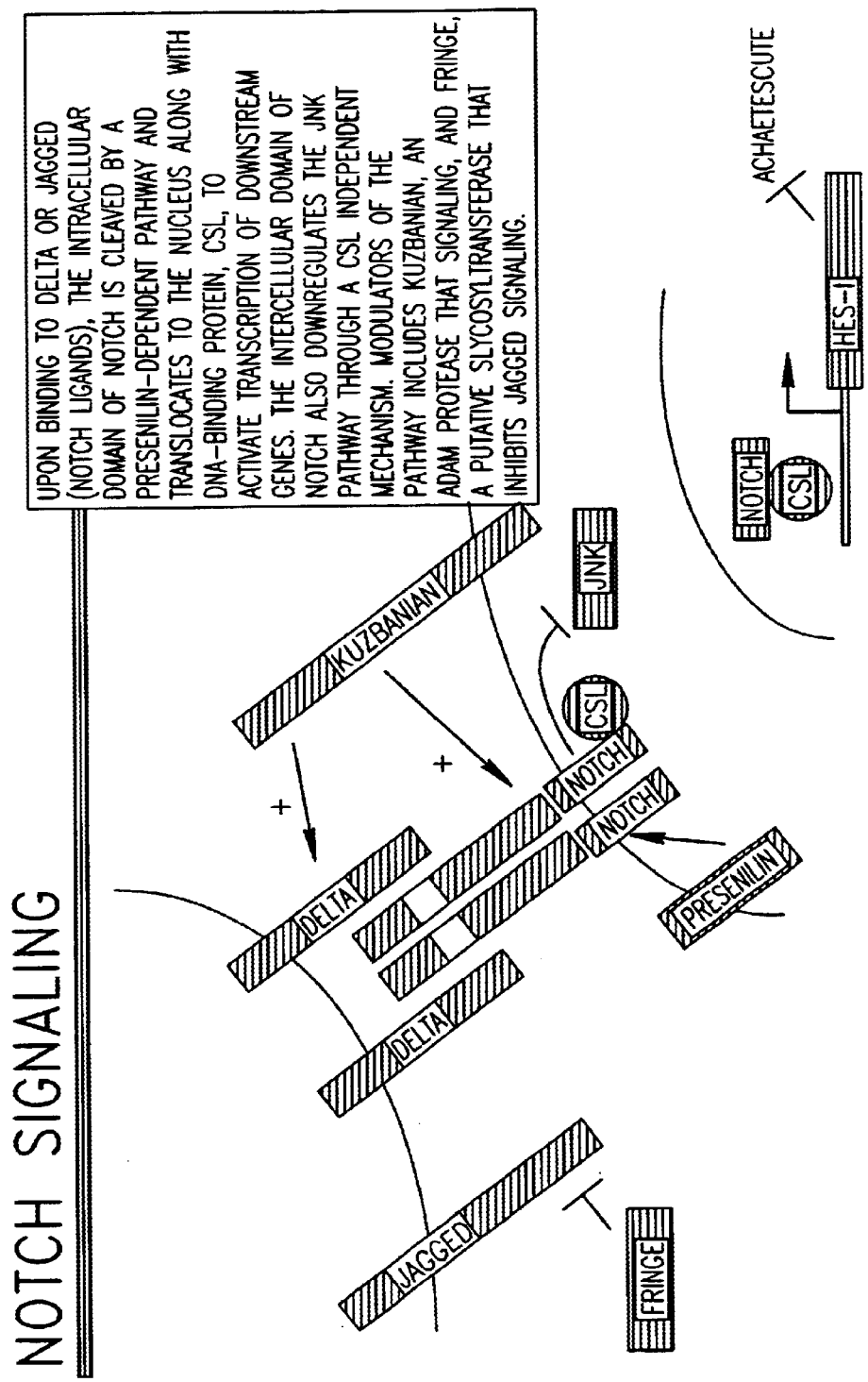
FIG. 7 is a diagram representing the interaction between the Notch receptor and the Notch ligands. Upon binding to Delta or Jagged (Notch ligands), the intracellular domain of Notch is cleaved by a presenilin-dependent pathway and translocates to the nucleus along with DNA-binding protein, CSL, to activate transcription of downstream genes. The intracellular domain of Notch also downregulates the Jun-Kinase (JNK) pathway through a CSL independent mechanism (Zecchini, V. et al., *Biol.* 9:460–499, 1999). Modulators of the pathway includes Kuzbanian, a disintegrin and metalloproteinase (ADAM) that positively regulate Notch signaling, and Fringe, a putative glycosyltransferase that inhibits Jagged signaling.

The present invention relates to nucleotide sequences of Notch ligands, the proteins encoded by the nucleotide sequences, and uses of the polynucleotides, proteins, fragments thereof, and antibodies specific for the proteins and polypeptides.

There is increasing evidence for a role of the Notch pathway in human disease. All of the components of the pathway have yet to be identified, but among those identified to date, mutations that affect their interaction with each other can lead to a variety of syndromes and pathological conditions.

A role for Notch-Jagged interaction in angiogenesis has been reported, based on studies with a model for angiogenesis, which measures bovine microvascular endothelial cell invasion into a collagen gel, through formation of a network of capillary-like tubes. (Zimrin, A. et al., *Jour. Biol. Chem.* 271:32499–32502, 1996.) Growth factors such as FGF and VEGF can be added to determine the effect of Notch and Notch ligands on growth factor-induced endothelial cell behavior and differentiation.

The Notch pathway is also implicated in the development and maturation of T cells, as described in Radtke, F. et al., *Immunity* 10:547–558, 1999. The Notch ligands of the invention are therefore useful candidates for modulating the immune system, including determining the fate of T cells, thereby affecting antibody production and/or cell-mediated immunity.

As discussed in detail below, the Notch ligands of the present invention can be used to further elucidate the role of the Notch pathway in human development and disease. In particular, the ligand gene referred to as 3md3 (SEQ ID NO:2) displays a pattern of tissue expression that overlaps with the endothelial cell-specific gene Notch 4. This has important implications for the use of 3md3 in modulating angiogenesis, such as preventing cancer-related angiogenesis to stop tumor growth and for therapeutic angiogenesis, e.g., to induce blood vessel formation in ischemia. A mouse mammary tumor virus (MMTV) oncogene, int-3, encodes the intracellular signaling domain of Notch 4. Thus, the MMTV may target angiogenesis as a component of its tumor promoting activity. (Zimrin, A. et al., *J. Biol. Chem.* 271:32499–32502, 1996.)

3md3 is therefore a candidate for regulating Notch 4-mediated angiogenesis. Without being bound by a particular mechanism, applicants believe that by modulating the interaction between Notch ligand 3md3 and its receptors, the growth and differentiation of microvascular endothelial cells can be regulated. The role of the 3md3 gene product in angiogenesis can be determined using a model of angiogenesis, for example as described in more detail in the Examples.

Identification of Novel Notch Receptor Ligands

Two new ligands of the Notch receptor have been identified, and are referred to as 3md3 and 2hd1.

1. 3md3. This gene is likely the human ortholog of murine Delta 3 (Dll3, GenBank protein ID 3721842). It is expressed in the heart, kidney, skeletal muscle and kidney as a 4.9 kb message. The nucleotide sequence for the full-length coding region (1752 basepairs) is disclosed in SEQ ID NO:1, and the encoded amino acid sequence (583 amino acids) is disclosed in SEQ ID NO:2.

The mouse Dll3 gene is predominantly expressed in the neuroectoderm and paraxial mesoderm during embryogenesis (Dunwoodie, S. L. et al., *Development* 124:3065–3076, 1997). The cDNA consists of 2243 basepairs, encoding a protein of 585 amino acids. FIG. 1 compares the polynucleotide sequences of 3md3 with murine Dll3. FIG. 1 also compares the sequence of a human Delta polynucleotide sequence disclosed in WO 98 45434-A1 (W80813). An examination of the alignments in FIG. 1 indicates that the novel sequence of the invention, 3md3, is more closely related to the mouse Delta 3 sequence than is the human Delta sequence. Therefore, it is believed that 3md3 is the human ortholog of the mouse Dll3 gene. The tissue expression of 3md3 overlaps with that of the endothelial-specific gene Notch 4, suggesting that it may be a functional ligand for Notch 4.

As described in more detail herein, the present invention provides new methods and materials for modulating angiogenesis and immune responses using products of 3md3.

2. 2hd1. This gene contains a region that is identical to the DSL (Delta/Serrate/Lag) domain in human Delta 1, followed by a divergent sequence of 24 amino acids and a stop codon. The DSL domain is a region of homology common to the known Notch ligand and is involved in receptor binding (Fitzgerald and Greenwald, *Development* 121:4275–4282, 1995). SEQ ID NO:3 represents the coding region of 2hd1, and SEQ ID NO:4 represents the translation of the coding region.

Polynucleotides

The invention relates to the specific polynucleotide sequences disclosed in SEQ ID NO:1 and 3, and to additional embodiments described herein. The polynucleotides of the invention also include polynucleotides having sequence similarity or sequence identity to SEQ ID NO:1 or 3. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g., allelic variants, genetically altered versions of the gene, etc., bind to one of the provided polynucleotide sequences (SEQ ID NOs:1 and 3) under stringent hybridization conditions. By using probes, particularly labeled probes of DNA sequences, one of skill can isolate homologous or related genes. The source of homologous genes can be any species, e.g., primate species, particularly human; rodents, such as rats and mice; canines, felines, bovines, ovines, equines, yeast, nematodes, etc.

Preferably, hybridization is performed using at least 15 contiguous nucleotides (nt) of at least one of SEQ ID NOs:1 and 3. That is, when at least 15 contiguous nt of one of the disclosed SEQ ID NOs is used as a probe, the probe will preferentially hybridize with a nucleic acid comprising the complementary sequence, allowing the identification and retrieval of the nucleic acids that uniquely hybridize to the selected probe. Probes of more than 15 nt can be used, e.g., probes of from about 18 nt to about 100 nt, but 15 nt represents sufficient sequence for unique identification.

The polynucleotides of the invention also include naturally occurring variants of the nucleotide sequences (e.g., degenerate variants, allelic variants). Variants of the polynucleotides of the invention are identified by hybridization of putative variants with nucleotide sequences disclosed herein, preferably by hybridization under stringent conditions. For example, by using appropriate wash conditions, variants of the polynucleotides of the invention can be identified where the allelic variant exhibits at most about 25–30% base pair (bp) mismatches relative to the selected polynucleotide probe. In general, allelic variants contain 15–25% bp mismatches, and can contain as little as even 5–15%, or 2–5%, or 1–2% bp mismatches, as well as a single bp mismatch.

The invention also encompasses homologs corresponding to the polynucleotides of SEQ ID NOs:1 and 3, where the source of homologous genes can be any mammalian species, e.g., primate species, particularly human; rodents, such as rats; canines, felines, bovines, ovines, equines, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as BLAST, described in Altschul et al., *J. Mol. Biol.* 215:403–10 (1990). For the purposes of this invention, a preferred method of calculating percent identity is the Smith-Waterman algorithm, using the following. Global DNA sequence identity is greater than 65% as determined by the Smith-Waterman homology search algorithm as implemented in MPSRCH program (Oxford Molecular) using an affine gap search with the following search parameters: gap open penalty, 12; and gap extension penalty, 1.

The subject nucleic acids can be cDNAs or genomic DNAs, as well as fragments thereof, particularly fragments that encode a biologically active gene product and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can also include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated polynucleotides and polynucleotide fragments of the invention comprise at least about 10, about 15, about 20, about 35, about 50, about 100, about 150 to about 200, about 250 to about 300, or about 350 contiguous nt selected from the polynucleotide sequences as shown in SEQ ID NOs:1 and 3. Such fragments are exemplary only, and include all intervening sizes, such as 11, 12, 13, etc.; 51, 52, 53, etc.; 151, 152, 153, etc., and so on. For the most part, fragments will be of at least 15 nt, usually at least 18 nt or 25 nt, and up to at least about 50 contiguous nt in length or more. In a preferred embodiment, the polynucleotide molecules comprise a contiguous sequence of at least 12 nt selected from the group consisting of the polynucleotides shown in SEQ ID NOs:1 and 3.

Preferred fragments are those which contain an antigenic determinant, and/or which are functionally active. "Functionally active" fragments include those with adhesive properties. Preferred fragments of 3md3 and/or 2hd1 include the full-length protein, an extracellular domain with a transmembrane region, and fragments of the proteins that are homologous or functionally equivalent to the adhesive fragments of Drosophila Delta mediating heterotypic (amino acids 1–230) or homotypic (32–320) interactions. Such fragments can be expressed independently or as fusion proteins. Fusion proteins may include myc-, HA-, or His6-tags. Fusion proteins may contain the Fc domain of human IgG.

Derivatives of Delta proteins, and assays for measuring the biological activity of the derivatives, are disclosed in WO 97/06571, which is incorporated by reference. WO 97/06571 also discloses therapeutics, including antisense compositions, based on or derived from polynucleotides encoding Delta proteins. Such methods and compositions are applicable to the novel ligands of the invention. Truncations of Notch ligands are disclosed in U.S. Pat. No. 5,648,464, which is incorporated by reference.

Probes specific to the polynucleotides of the invention can be generated using the polynucleotide sequences disclosed in SEQ ID NOs:1 and 3. The probes are preferably at least about a 12, 15, 16, 18, 20, 22, 24, or 25 nt fragment of a corresponding contiguous sequence of SEQ ID NOs:1 and 3, and can be less than 2, 1, 0.5, 0.1, or 0.05 kb in length. The probes can be synthesized chemically or can be generated from longer polynucleotides using restriction enzymes. The probes can be labeled, for example, with a radioactive, biotinylated, or fluorescent tag.

The polynucleotides of the subject invention are isolated and obtained in substantial purity, generally as other than an intact chromosome. Usually, the polynucleotides, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The polynucleotides of the invention can be provided as a linear molecule or within a circular molecule, and can be provided within autonomously replicating molecules (vectors) or within molecules without replication sequences. Expression of the polynucleotides can be regulated by their own or by other regulatory sequences known in the art. The polynucleotides of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The subject nucleic acid compositions can be used, for example, to produce polypeptides, as probes for the detection of mRNA of the invention in biological samples (e.g., extracts of human cells), to generate additional copies of the polynucleotides, to generate ribozymes or antisense oligonucleotides, and as single stranded DNA probes or as triple-strand forming oligonucleotides. The probes described herein can be used to, for example, determine the presence or absence of the polynucleotide sequences as shown in SEQ ID NOs:1 and 3 or variants thereof in a sample. These and other uses are described in more detail below.

Polypeptide Fragments

The invention provides polypeptide fragments of the disclosed protein. Polypeptide fragments of the invention can comprise at least 8, 10, 12, 15, 18, 19, 20, 25, 50, 75, 100, 125, 130, 140, 150, 160, 170, 180, 190, 200, 250, 300, 350, 400, 450, 500, 550, 560, 570 or 580 contiguous amino acids from SEQ ID NO:2. Also included are all intermediate length fragments in this range, such as 101, 102, 103, etc.; 170, 171, 172, etc.; and 600, 601, 601, etc. The specific lengths listed herein are exemplary only and not limiting. The invention also provides fragments of at least 81 contiguous amino acids from SEQ ID NO:4.

Biologically Active Variants

Variants of the protein and polypeptides disclosed herein can also occur. Variants can be naturally or non-naturally occurring. Naturally occurring variants are found in humans or other species and comprise amino acid sequences which are substantially identical to the amino acid sequence shown in SEQ ID NO:2 or 4. Species homologs of the protein can be obtained using subgenomic polynucleotides of the invention, as described below, to make suitable probes or primers to screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants, specifically the four transmembrane configuration and the interaction with other cell surface proteins, are also included here. Preferably, naturally or non-naturally occurring variants have amino acid sequences which are at least 85%, 90%, or 95% identical to the amino acid sequence shown in SEQ ID NO:2 or 4. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

Guidance in determining which amino acid residues can be substituted, inserted, or deleted without abolishing biological or immunological activity can be found using computer programs well known in the art, such as DNASTAR software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant.

Variants of the 3md3 and/or 2hd1 proteins disclosed herein include glycosylated forms, aggregative conjugates with other molecules, and covalent conjugates with unrelated chemical moieties. Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314.

Preferably, amino acid changes in the 3md3 and/or 2hd1 protein or polypeptide variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of 3md3 and/or 2hd1 protein or polypeptide variants are of the same type as a protein comprising the amino acid sequence encoded by the nucleotide sequence shown in SEQ ID NO:2 or 4, respectively, although the properties and functions of variants can differ in degree. 3md3 and/or 2hd1 protein variants include glycosylated forms, aggregative conjugates with other molecules, and covalent conjugates with unrelated chemical moieties. 3md3 and/or 2hd1 protein variants also include allelic variants, species variants, and muteins. Truncations or deletions of regions which do not affect the differential expression of the 3md3 and/or 2hd1 genes are also variants. Covalent variants can be prepared by linking functionalities to groups which are found in the amino acid chain or at the N- or C-terminal residue, as is known in the art.

It will be recognized in the art that some amino acid sequence of the 3md3 and/or 2hd1 proteins of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., Nature 361:266–268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the 3md3 and/or 2hd1 polypeptides which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," Science 247:1306–1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

Amino acids in the polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Fusion Proteins

Fusion proteins comprising proteins or polypeptide fragments of 3md3 and/or 2hd1 can also be constructed. Fusion proteins are useful for generating antibodies against amino acid sequences and for use in various assay systems. For example, fusion proteins can be used to identify proteins which interact with a protein of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence and/or a transmembrane domain of 3md3 and/or 2hd1 or a fragment thereof can be used to target other protein domains to cellular locations in which the domains are not normally found, such as bound to a cellular membrane or secreted extracellularly.

A fusion protein comprises two protein segments fused together by means of a peptide bond. Amino acid sequences for use in fusion proteins of the invention can be utilize the amino acid sequence shown in SEQ ID NO:2 or 4 or can be prepared from biologically active variants of SEQ ID NO:2 or 4, such as those described above. The first protein segment can include of a full-length 3md3 and/or 2hd1.

Other first protein segments can consist of at least 8, 10, 12, 15, 18, 19, 20, 25, 50, 75, 100, 125, 130, 140, 150, 160, 170, 180, 190, 200, 250, 300, 350, 400, 450, 500, 550, 560, 570 or 580 contiguous amino acids from SEQ ID NO:2.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding sequence of SEQ ID NO:1 or 3 in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolation and Production of 3md3

3md3 is expressed in human microvascular endothelial cells and can be extracted from these cells or from other human cells, such as recombinant cells comprising SEQ ID NO:1 using standard biochemical methods. These methods include, but are not limited to, size exclusion chromatography, ammonium sulfate fractionation, ion exchange chromatography, affinity chromatography, crystallization, electrofocusing, and preparative gel electrophoresis. The isolated and purified protein or polypeptide is separated from other compounds which normally associate with the protein or polypeptide in a cell, such as other proteins, carbohydrates, lipids, or subcellular organelles. A preparation of isolated and purified protein or polypeptide is at least 80% pure; preferably, the preparations are 90%, 95%, or 99% pure. Purity of the preparations can be assessed by any means known in the art. For example, the purity of a preparation can be assessed by examining electrophoretograms of protein or polypeptide preparations at several pH values and at several polyacrylamide concentrations, as is known in the art.

Proteins, fusion proteins, or polypeptides of the invention can be produced by recombinant DNA methods. For production of recombinant proteins, fusion proteins, or polypeptides, a coding sequence of the nucleotide sequence shown in SEQ ID NO:1 or 3 can be expressed in prokaryotic or eukaryotic host cells using expression systems known in the art. These expression systems include bacterial, yeast, insect, and mammalian cells.

The resulting expressed 3md3 and/or 2hd1 proteins can then be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired protein or polypeptide is typically greater than 95% pure. Further purification can be undertaken, using, for example, any of the techniques listed above.

It may be necessary to modify a protein produced in yeast or bacteria, for example by phosphorylation or glycosylation of the appropriate sites, in order to obtain a functional protein. Such covalent attachments can be made using known chemical or enzymatic methods.

3md3 and/or 2hd1 protein or polypeptide of the invention can also be expressed in cultured host cells in a form which will facilitate purification. For example, a protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen. Proteins, fusion proteins, or polypeptides can also be tagged with an epitope, such as a "Flag" epitope (Kodak), and purified using an antibody which specifically binds to that epitope.

The coding sequence disclosed herein can also be used to construct transgenic animals, such as cows, goats, pigs, or sheep. Female transgenic animals can then produce proteins, polypeptides, or fusion proteins of the invention in their milk. Methods for constructing such animals are known and widely used in the art.

Alternatively, synthetic chemical methods, such as solid phase peptide synthesis, can be used to synthesize a secreted protein or polypeptide. General means for the production of peptides, analogs or derivatives are outlined in Chemistry and Biochemistry of Amino Acids, Peptides, and Proteins—A Survey of Recent Developments, B. Weinstein, ed. (1983). Substitution of D-amino acids for the normal L-stereoisomer can be carried out to increase the half-life of the molecule. Variants can be similarly produced.

Isolated genes corresponding to the cDNA sequences disclosed herein are also provided. Standard molecular biology methods can be used to isolate the corresponding genes using the cDNA sequences provided herein. These methods include preparation of probes or primers from the nucleotide sequence shown in SEQ ID NO:1 or 3 for use in identifying or amplifying the genes from human genomic libraries or other sources of human genomic DNA.

Polynucleotide molecules of the invention can also be used as primers to obtain additional copies of the polynucleotides, using polynucleotide amplification methods. Polynucleotide molecules can be propagated in vectors and cell lines using techniques well known in the art. Polynucleotide molecules can be on linear or circular molecules. They can be on autonomously replicating molecules or on molecules without replication sequences. They can be regulated by their own or by other regulatory sequences, as is known in the art.

Polynucleotide Constructs

Polynucleotide molecules comprising the coding sequences disclosed herein can be used in a polynucleotide construct, such as a DNA or RNA construct. Polynucleotide molecules of the invention can be used, for example, in an expression construct to express all or a portion of a secreted protein, variant, fusion protein, or single-chain antibody in a host cell. An expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the desired protein. The polynucleotide segment is located downstream from the promoter. Transcription of the polynucleotide segment initiates at the promoter. The expression construct can be linear or circular and can contain sequences, if desired, for autonomous replication.

Host Cells

An expression construct can be introduced into a host cell. The host cell comprising the expression construct can be any suitable prokaryotic or eukaryotic cell. Expression systems in bacteria include those described in Chang et al., *Nature* (1978) 275: 615; Goeddel et al., *Nature* (1979) 281: 544; Goeddel et al., *Nucleic Acids Res.* (1980) 8: 4057; EP 36,776; U.S. Pat. No. 4,551,433; deBoer et al., *Proc. Natl. Acad. Sci. USA* (1983) 80: 21–25; and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J Basic Microbiol.* (1985) 25: 141; Gleeson et al., *J. Gen. Microbiol.* (1986) 132: 3459, Roggenkamp et al., *Mol. Gen. Genet.* (1986) 202:302); Das et al., *J Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376; U.S. Pat. No. 4,837,148; U.S. Pat. No. 4,929,555; Beach and Nurse, *Nature* (1981) 300: 706; Davidow et al., *Curr. Genet.* (1985) 1p: 380; Gaillardin et al., *Curr. Genet.* (1985) 10: 49; Ballance et al., *Biochem. Biophys. Res. Commun.* (1983) 112: 284–289; Tilbum et al., *Gene* (1983) 26: 205–22;, Yelton et al., *Proc. Natl. Acad. Sci. USA* (1984) 81: 1470–1474; Kelly and Hynes, *EMBO J.* (1985) 4: 475479; EP 244,234; and WO 91/00357.

Expression of heterologous genes in insects can be accomplished as described in U.S. Pat. No. 4,745,051; Friesen et al. (1986) "The Regulation of Baculovirus Gene Expression" in: THE MOLECULAR BIOLOGY OF BACULOVIRUSES (W. Doerfler, ed.); EP 127,839; EP 155,476; Vlak et al., *J. Gen. Virol.* (1988) 69: 765–776; Miller et al., *Ann. Rev. Microbiol.* (1988) 42: 177; Carbonell et al., *Gene* (1988) 73: 409; Maeda et al., *Nature* (1985) 315: 592–594; Lebacq-Verheyden et al., *Mol. Cell Biol.* (1988) 8: 3129; Smith et al., *Proc. Natl. Acad. Sci. USA* (1985) 82: 8404; Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENERIC ENGINEERING (Setlow, J. K. et al. eds.), Vol. 8 (Plenum Publishing, 1986), pp. 277–279; and Maeda et al., *Nature*, (1985) 315: 592–594.

Mammalian expression can be accomplished as described in Dijkema et al., *EMBO J.* (1985) 4: 761; Gorman et al., *Proc. Natl. Acad. Sci. USA* (1982b) 79: 6777; Boshart et al., *Cell* (1985) 41: 521; and U.S. Pat. No. 4,399,216. Other features of mammalian expression can be facilitated as described in Ham and Wallace, *Meth Enz.* (1979) 58: 44; Barnes and Sato, *Anal. Biochem.* (1980) 102: 255; U.S. Pat. No. 4,767,704; U.S. 4,657,866; U.S. Pat. No. 4,927,762; U.S. Pat. No. 4,560,655; WO 90/103430, WO 87/00195, and U.S. RE Pat. No. 30,985.

Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Expression of an endogenous gene encoding a protein of the invention can also be manipulated by introducing by homologous recombination a DNA construct comprising a transcription unit in frame with the endogenous gene, to form a homologously recombinant cell comprising the transcription unit. The transcription unit comprises a targeting sequence, a regulatory sequence, an exon, and an unpaired splice donor site. The new transcription unit can be used to turn the endogenous gene on or off as desired. This method of affecting endogenous gene expression is taught in U.S. Pat. No. 5,641,670.

The targeting sequence is a segment of at least 10, 12, 15, 20, or 50 contiguous nucleotides from the nucleotide sequence shown in SEQ ID NO:1 or 3. The transcription unit is located upstream to a coding sequence of the endogenous gene. The exogenous regulatory sequence directs transcription of the coding sequence of the endogenous gene.

Expression of Polypeptide Encoded by Full-Length cDNA or Full-Length Gene

The provided polynucleotides (e.g., a polynucleotide having a sequence of one of SEQ ID NOs:1 and 3), the corresponding cDNA, or the full-length gene is used to express a partial or complete gene product. Constructs of polynucleotides having sequences of SEQ ID NOs:1 and 3 can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49–53. In this method, assembly PCR (the synthesis of long DNA sequences from large numbers of oligodeoxyribonucleotides) is derived from DNA shuffling (Stemmer, *Nature* (1994) 370:389–391).

Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y. The gene product encoded by a polynucleotide of the invention is expressed in any expression system, including, for example, bacterial, yeast, insect, amphibian and mammalian systems. Vectors, host cells and methods for obtaining expression in same are well known in the art. Suitable vectors and host cells are described in U.S. Pat. No. 5,654,173.

Polynucleotide molecules comprising a polynucleotide sequence provided herein are generally propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. Methods for preparation of vectors comprising a desired sequence are well known in the art.

The polynucleotides set forth in SEQ ID NOs:1 and 3 or their corresponding full-length polynucleotides are linked to regulatory sequences as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used.

When any appropriate host cells or organisms are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Expression of a gene corresponding to SEQ ID NO:1 or 3 can be regulated in the cell to which the gene is native. For example, an endogenous gene of a cell can be regulated by an exogenous regulatory sequence as disclosed in U.S. Pat. No. 5,641,670.

Antibody Production

Expression products of a polynucleotide of the invention, as well as the corresponding mRNA, cDNA, or full gene, can be prepared and used for raising anti-bodies for experimental, diagnostic, and therapeutic purposes. For example, antibodies can be generated using fusion proteins or peptide sequences derived from the corresponding protein. The polynucleotide or related cDNA is expressed as described above, and antibodies are prepared. These antibodies are specific to an epitope on the polypeptide encoded by the polynucleotide, and can precipitate or bind to the corresponding native protein in a cell or tissue preparation or in a cell-free extract of an in vitro expression system.

Methods for production of monoclonal and polyclonal antibodies that specifically bind a selected antigen are well known in the art. Typically, at least 6, 8, 10, or 12 contiguous amino acids are required to form an epitope. Epitopes that involve non-contiguous amino acids may require a longer polypeptide, e.g., at least 15, 25, or 50 amino acids. Antibodies that specifically bind to human polypeptides encoded by the provided polynucleotides should provide a detection signal at least 5-, 10-, or 20-fold higher than a detection signal provided with other proteins when used in Western blots or other immunochemical assays. Preferably, antibodies that specifically bind poly-peptides of the invention do not bind to other proteins in immunochemical assays at detectable levels and can immunoprecipitate the specific polypeptide from solution.

The invention also contemplates naturally occurring antibodies specific for a polypeptide of the invention. For example, serum antibodies to a polypeptide of the invention in a human population can be purified by methods well known in the art, e.g., by passing antiserum over a column to which the corresponding selected polypeptide or fusion protein is bound. The bound antibodies can then be eluted from the column, for example using a buffer with a high salt concentration.

In addition to the antibodies discussed above, the invention also contemplates genetically engineered antibodies, antibody derivatives (e.g., single chain antibodies, antibody fragments (e.g., Fab, etc.)), according to methods well known in the art.

In certain embodiments of the present invention, humanized anti-3md3 or 2hd1 monoclonal antibodies are provided. The phrase "humanized antibody" refers to an antibody derived from a non-human antibody, typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522–525 (1986); Morrison et al., *Proc. Natl. Acad. Sci., U.S.A.*, 81:6851–6855 (1984); Morrison and Oi, *Adv. Immunol.*, 44:65–92 (1988); Verhoeyer et al., *Science* 239:1534–1536 (1988); Padlan, *Molec. Immun.* 28:489–498 (1991); Padlan, *Molec. Immzinol.* 31(3):169–217 (1994); and Kettleborough, C. A. et al., *Protein Eng.* 4(7):773–83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901–917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which patents are incorporated herein by reference.

Humanized antibodies to 3md3 and/or 2hd1 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFá, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

In the present invention, 3md3 and/or 2hd1 polypeptides of the invention and variants thereof are used to immunize a transgenic animal as described above. Monoclonal antibodies are made using methods known in the art, and the specificity of the antibodies is tested using corresponding isolated 3md3 and/or 2hd1 polypeptides.

Polynucleotides or Arrays for Diagnostics

Polynucleotide arrays are created by spotting polynucleotide probes onto a substrate (e.g., glass, nitrocellose, etc.) in a two-dimensional matrix or array having bound probes. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays can be used to detect differential expression of a polynucleotide between a test cell and control cell (e.g., cancer cells and normal cells). For example, high expression of a particular message in a cancer cell, which is not observed in a corresponding normal cell, can indicate a cancer specific gene product. Exemplary uses of arrays are further described in, for example, Pappalarado et al., *Sem. Radiation Oncol.* (1998) 8:217; and Ramsay, *Nature Biotechnol.* (1998) 16:40.

Differential Expression in Diagnosis

The polynucleotides of the invention can also be used to detect differences in expression levels between two cells, e.g., as a method to identify abnormal or diseased tissue in a human. In general, the expression of a gene corresponding to a specific polynucleotide is compared between a first tissue that is suspected of being diseased and a second, normal tissue of the human. The tissue suspected of being abnormal or diseased can be derived from a different tissue type of the human, but preferably it is derived from the same tissue type; for example an intestinal polyp or other abnormal growth should be compared with normal intestinal tissue. The normal tissue can be the same tissue as that of the test sample, or any normal tissue of the patient, especially those that express the polynucleotide-related gene of interest (e.g., brain, thymus, testis, heart, prostate, placenta, spleen, small intestine, skeletal muscle, pancreas, breast, ovary, lung, and the mucosal lining of the colon). A difference between the polynucleotide-related gene, mRNA, or protein in the two tissues which are compared, for example in molecular weight, amino acid or nucleotide sequence, or relative abundance, indicates a change in the gene, or a gene which regulates it, in the tissue of the human that was suspected of being diseased. Examples of detection of differential expression and its use in diagnosis of cancer are described in U.S. Pat. Nos. 5,688,641 and 5,677,125.

Because mutations and defects in the Notch pathway are implicated in developmental disorders, a genetic predisposition to Notch pathway-related disease in a human can also be detected by comparing expression levels of an mRNA or protein corresponding to a polynucleotide of the invention in a fetal tissue, with levels in normal fetal tissue. Fetal tissues that are used for this purpose include, but are not limited to, amniotic fluid, chorionic villi, blood, and the blastomere of an in vitro-fertilized embryo. The comparable normal polynucleotide-related gene is obtained from any tissue. The mRNA or protein is obtained from a normal tissue of a human in which the polynucleotide-related gene is expressed. Differences such as alterations in the nucleotide sequence or size of the same product of the fetal polynucleotide-related gene or mRNA, or alterations in the molecular weight, amino acid sequence, or relative abundance of fetal protein, can indicate a germline mutation in the polynucleotide-related gene of the fetus, which indicates a genetic predisposition to disease.

In general, diagnostic, prognostic, and other methods of the invention based on differential expression involve detection of a level or amount of a gene product, particularly a differentially expressed gene product, in a test sample obtained from a patient suspected of having or being susceptible to a disease (e.g., breast cancer, lung cancer, colon cancer and/or metastatic forms thereof), and comparing the detected levels to those levels found in normal cells (e.g., cells substantially unaffected by cancer) and/or other control cells (e.g., to differentiate a cancerous cell from a cell affected by dysplasia). Furthermore, the severity of the disease can be assessed by comparing the detected levels of a differentially expressed gene product with those levels detected in samples representing the levels of differentially gene product associated with varying degrees of severity of disease. It should be noted that use of the term "diagnostic" herein is not necessarily meant to exclude "prognostic" or "prognosis," but rather is used as a matter of convenience.

The term "differentially expressed gene" is generally intended to encompass a polynucleotide that can, for example, include an open reading frame encoding a gene product (e.g., a polypeptide), and/or introns of such genes and adjacent 5' and 3' non-coding nucleotide sequences involved in the regulation of expression, up to about 20 kb beyond the coding region, but possibly further in either direction. The gene can be introduced into an appropriate vector for extrachromosomal maintenance or for integration into a host genome. In general, a difference in expression level associated with a decrease in expression level of at least about 25%, usually at least about 50% to 75%, more usually at least about 90% or more is indicative of a differentially expressed gene of interest, i.e., a gene that is underexpressed or down-regulated in the test sample relative to a control sample. Furthermore, a difference in expression level associated with an increase in expression of at least about 25%, usually at least about 50% to 75%, more usually at least about 90% and can be at least about 1½-fold, usually at least about 2-fold to about 10-fold, or about 100-fold to about 1,000-fold increase relative to a control sample is indicative of a differentially expressed gene of interest, i.e., an overexpressed or up-regulated gene.

"Differentially expressed polynucleotide" as used herein means a nucleic acid molecule (RNA or DNA) comprising a sequence that represents a differentially expressed gene, e.g., the differentially expressed polynucleotide comprises a sequence (e.g., an open reading frame encoding a gene product) that uniquely identifies a differentially expressed gene so that detection of the differentially expressed polynucleotide in a sample is correlated with the presence of a differentially expressed gene in a sample. "Differentially expressed polynucleotides" is also meant to encompass fragments of the disclosed polynucleotides, e.g., fragments retaining biological activity, as well as nucleic acids homologous, substantially similar, or substantially identical (e.g., having about 90% sequence identity) to the disclosed polynucleotides.

"Diagnosis" as used herein generally includes determination of a subject's susceptibility to a disease or disorder, determination as to whether a subject is presently affected by a disease or disorder, as well as the prognosis of a subject affected by a disease or disorder (e.g., identification of pre-metastatic or metastatic cancerous states, stages of cancer, or responsiveness of cancer to therapy).

"Sample" or "biological sample" as used throughout here are generally meant to refer to samples of biological fluids or tissues, particularly samples obtained from tissues, especially from cells of the type associated with the disease for which the diagnostic application is designed, and the like. "Samples" is also meant to encompass derivatives and fractions of such samples (e.g., cell lysates). Where the sample is solid tissue, the cells of the tissue can be dissociated or tissue sections can be analyzed.

Methods of the subject invention useful in diagnosis or prognosis typically involve comparison of the abundance of a selected differentially expressed gene product in a sample of interest with that of a control to determine any relative differences in the expression of the gene product, where the difference can be measured qualitatively and/or quantitatively. Quantitation can be accomplished, for example, by comparing the level of expression product detected in the sample with the amounts of product present in a standard curve. A comparison can be made visually; by using a technique such as densitometry, with or without computerized assistance; by preparing a representative library of cDNA clones of mRNA isolated from a test sample, sequencing the clones in the library to determine that number of cDNA clones corresponding to the same gene product, and analyzing the number of clones corresponding to that same gene product relative to the number of clones of the same gene product in a control sample; or by using an array to detect relative levels of hybridization to a selected sequence or set of sequences, and comparing the hybridization pattern to that of a control. The differences in expression are then correlated with the presence or absence of an abnormal expression pattern. Various methods for determining the nucleic acid abundance in a sample are known to those of skill in the art (see, e.g., WO 97/27317). In general, diagnostic assays of the invention involve detection of a gene product of the polynucleotide sequence (e.g., mRNA or polypeptide) that corresponds to a sequence of SEQ ID NOs:1 and 3. The patient from whom the sample is obtained can be apparently healthy, susceptible to disease (e.g., as determined by family history or exposure to certain environmental factors), or can already be identified as having a condition in which altered expression of a gene product of the invention is implicated.

Diagnosis can be determined based on detected gene product expression levels of a gene product encoded by at least one of the polynucleotides having a sequence set forth in SEQ ID NOs:1 and 3, and can involve detection of expression of genes corresponding to all of SEQ ID NOs:1 and 3 and/or additional sequences that can serve as additional diagnostic markers and/or reference sequences. Where the diagnostic method is designed to detect the presence or susceptibility of a patient to cancer, the assay preferably involves detection of a gene product encoded by a gene corresponding to a polynucleotide that is differentially expressed in cancer.

Any of a variety of detectable labels can be used in connection with the various embodiments of the diagnostic methods of the invention. Suitable detectable labels include fluorochromes, (e.g., fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g., $^{32}$P, 35S, $^{3}$H, etc.), and the like. The detectable label can involve a two stage systems (e.g., biotin-avidin, hapten-anti-hapten antibody, etc.)

Reagents specific for the polynucleotides and polypeptides of the invention, such as antibodies and nucleotide probes, can be supplied in a kit for detecting the presence of an expression product in a biological sample. The kit can also contain buffers or labeling components, as well as instructions for using the reagents to detect and quantify expression products in the biological sample. Exemplary embodiments of the diagnostic methods of the invention are described below in more detail.

Polypeptide detection in diagnosis. In one embodiment, the test sample is assayed for the level of a differentially expressed polypeptide. Diagnosis can be accomplished using any of a number of methods to determine the absence or presence or altered amounts of the differentially expressed polypeptide in the test sample. For example, detection can utilize staining of cells or histological sections with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas red, etc.). The absence or presence of antibody binding can be determined by various methods, including flow cytometry of dissociated cells, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

mRNA detection. The diagnostic methods of the invention can also or alternatively involve detection of mRNA encoded by the 3md3 and/or 2hd1 gene. Any suitable qualitative or quantitative methods known in the art for detecting specific mRNAs can be used. mRNA can be detected by, for example, in situ hybridization in tissue sections, by reverse transcriptase-PCR, or in Northern blots containing poly A+ mRNA. One of skill in the art can readily use these methods to determine differences in the size or amount of mRNA transcripts between two samples. mRNA expression levels in a sample can also be determined by generation of a library of expressed sequence tags (ESTs) from the sample, where the EST library is representative of sequences present in the sample (Adams, et al., (1991) *Science* 252:1651). Enumeration of the relative representation of ESTs within the library can be used to approximate the relative representation of the gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein. Alternatively, gene expression in a test sample can be performed using serial analysis of gene expression (SAGE) methodology (e.g., Velculescu et al., *Science* (1995) 270:484), differential display methodology (see, e.g., U.S. Pat. Nos. 5,776,683 and 5,807,680), or DNA microarray methodology.

Alternatively, gene expression can be analyzed using hybridization analysis. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample.

Use of a single gene in diagnostic applications. The diagnostic methods of the invention can focus on the expression of a single differentially expressed gene represented by SEQ ID NO:1 or 3. For example, the diagnostic method can involve detecting a differentially expressed gene, or a polymorphism of such a gene (e.g., a polymorphism in a coding region or control region), that is associated with disease. Disease-associated polymorphisms can include deletion or truncation of the gene, mutations that alter expression level and/or affect binding specificity, such as interaction of the encoded protein with Notch receptor.

A number of methods are available for analyzing nucleic acids for the presence of a specific sequence, e.g., a disease associated polymorphism. Where large amounts of DNA are available, genomic DNA is used directly. Alternatively, the region of interest is cloned into a suitable vector and grown in sufficient quantity for analysis. Cells that express a differentially expressed gene can be used as a source of mRNA, which can be assayed directly or reverse transcribed into cDNA for analysis. The nucleic acid can be amplified by conventional techniques, such as the polymerase chain reaction (PCR), to provide sufficient amounts for analysis, and a detectable label can be included in the amplification reaction (e.g., using a detectably labeled primer or detectably labeled oligonucleotides) to facilitate detection. Alternatively, various methods are also known in the art that utilize oligonucleotide ligation as a means of detecting polymorphisms, see, e.g., Riley et al., *Nucl. Acids Res.* (1990) 18:2887; and Delahunty et al., *Am. J. Hum. Genet.* (1996) 58:1239.

The amplified or cloned sample nucleic acid can be analyzed by one of a number of methods known in the art. The nucleic acid can be sequenced by dideoxy or other methods, and the sequence of bases compared to a selected sequence, e.g., to a wild-type sequence. Hybridization with the polymorphic or variant sequence can also be used to determine its presence in a sample (e.g., by Southern blot, dot blot, etc.). The hybridization pattern of a polymorphic or variant sequence and a control sequence to an array of oligonucleotide probes immobilized on a solid support, as described in U.S. Pat. No. 5,445,934, or in WO 95/35505, can also be used as a means of identifying polymorphic or variant sequences associated with disease. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in a gene can be based on the functional or antigenic characteristics of the protein. Protein truncation assays are useful in detecting deletions that can affect the biological activity of the protein. Various immunoassays designed to detect polymorphisms in proteins can be used in screening. Where many diverse genetic mutations lead to a particular disease phenotype, functional protein assays have proven to be effective screening tools. The activity of the encoded protein can be determined by comparison with the wild-type protein.

Use of Polypeptides to Screen for Peptide Analogs and Antagonists

Polypeptides encoded by SEQ ID NOs:1 and 3 or by the corresponding full length genes can be used to screen peptide libraries to identify binding partners, such as ligands and receptors, from among the encoded polypeptides. Peptide libraries can be synthesized according to methods known in the art (see, e.g., U.S. Pat. No. 5,010,175, and WO 91/17823). Screening methods may include, but are not limited to, yeast two-hybrid screens, protein co-immunoprecipitation assays, and lambda gt11 expression library screening. Agonists or antagonists of the polypeptides of the invention can be screened using assay conditions that ideally resemble the conditions under which the native activity, i.e. interaction between Notch receptor and Notch ligand, is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native ligand can require concentrations equal to or greater than the native concentration, while inhibitors capable of binding irreversibly to the ligand can be added in concentrations on the order of the native concentration. In a non-limiting example, a peptide analog or antagonist would be tested for its ability to affect interaction between a ligand of the invention and a Notch receptor.

Pharmaceutical Compositions and Therapeutic Uses

Pharmaceutical compositions of the invention can comprise polypeptides, antibodies, or polynucleotides (including antisense nucleotides and ribozymes) of the claimed invention in a therapeutically effective amount. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the polynucleotide constructs in the individual to which it is administered. A non-limiting example of a pharmaceutical composition is a composition that either enhances or diminishes binding of Notch to a ligand comprising a polypeptide of SEQ ID NO:2 and 4 or fragment thereof. Where the ligand/Notch interaction promotes a disease-related process, interference with the interaction would be the goal of the therapy. If normal ligand/Notch interaction does not occur because of a defect in one or the other protein, then use of a composition that restores normal function is appropriate.

In other instances it may be desirable to promote angiogenesis, for example in wound healing and in therapeutic angiogenesis, for example to treat ischemia.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., New Jersey, 1991).

Delivery Methods. Once formulated, the compositions of the invention can be (1) administered directly to the subject (e.g., as polynucleotides or polypeptides); or (2) delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, myocardial, intratumoral, peritumoral, or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide (s) in liposomes, direct microinjection of the DNA into nuclei, and viral-mediated, such as adenovirus or alphavirus, all well known in the art.

In a preferred embodiment, disorders of proliferation, such as tumor-associated angiogenesis, can be amenable to treatment by administration of a therapeutic agent based on the provided polynucleotide, corresponding polypeptide or other corresponding molecule (e.g., antisense, ribozyme), agonist, or antagonist. The therapeutic agent can be administered in conjunction with one or more other agents including but not limited to FGF, VEGF, angiopoietin, angiogenin, and thrombopoietin. Administered "in conjunction" includes administration at the same time, or within 1 day, 12 hours, 6 hours, one hour, or less than one hour, as the other therapeutic agent(s). The compositions may be mixed for co-administration, or may be administered separately by the same or different routes.

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. The therapeutic polynucleotide composition can contain an expression construct comprising a promoter operably linked to a polynucleotide of at least 12, 22, 25, 30, or 35 contiguous nucleotides of the polynucleotides disclosed herein. Various methods can be used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. (USA)* (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the antisense subgenomic polynucleotides. Where greater expression is desired over a larger area of tissue, larger amounts of antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The present invention also relates to antisense oligonucleotides designed to interfere with the normal function of 3md3 and/or 2hd1 polynucleotides. Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550, 111; 5,563,253; 5,571,799; 5,587,361, 5,625,050 and 5,958, 773.

The antisense compounds of the invention can include modified bases as disclosed in 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567, 810, 5,574,142, 5,585,481, 5,587,371, 5,597,696 and 5,958, 773.

Chimeric antisense oligonucleotides are also within the scope of the invention, and can be prepared from the present inventive oligonucleotides using the methods described in, for example, U.S. Pat. Nos. 5,013,830, 5,149,797, 5,403, 711, 5,491,133, 5,565,350, 5,652,355, 5,700,922 and 5,958, 773.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth or viability as is known in the art.

According to the invention, antisense oligonucleotides can be added to cultures of endothelial cells, and the effect on endothelial cell invasion can be determined, in order to identify antisense compositions useful for in vivo use.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., *T.I.B.S.* 23:45–50, 1998.)

The therapeutic polynucleotides and polypeptides of the present invention can be delivered using gene delivery vehicles. The gene delivery vehicle can be of viral or non-viral origin (see generally, Jolly, *Cancer Gene Therapy*

(1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* 264:16985 (1989)); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* 14:2411 (1994), and in Woffendin, *Proc. Natl. Acad. Sci.* (1994) 91:11581–11585.

Further non-viral delivery suitable for use includes mechanical delivery systems such as the approach described in Woffendin et al., *Proc. Natl. Acad. Sci. USA* 91(24):11581 (1994). Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

The present invention will now be illustrated by reference to the following examples which set forth particularly advantageous embodiments. However, it should be noted that these embodiments are illustrative and are not to be construed as restricting the invention in any way.

EXAMPLES

Example 1

Identification and Analysis of Novel Notch Ligands

Two ligands for the human Notch receptor have been identified, sequenced, and analyzed using Northern blots and in situ hybridization.

A. 3md3

The first ligand is a 583 amino acid protein encoded by SEQ ID NO:1. The sequences are shown in FIG. 5, and the ligand is referred to as 3md3.

On the basis of alignment with the mouse Delta 3 amino acid sequence, 3md3 is putatively identified as the human ortholog of mouse Delta 3 (FIG. 1). Although a patent publication has identified a human "Delta 3" (WO 98 45434-A1), comparison of its alignment to mouse Delta 3, with 3md3 alignment to mouse Delta 3, indicates that 3md3 bears closer resemblance based on both amino acid (FIG. 1) and polynucleotide (FIG. 3) comparisons.

The expression of 3md3 in human tissues was investigated using an EST AI363919 (Image Clone No.2016425) as a probe. The results from the Northern blot indicate that 3md3 was expressed as a 4.9 kb message in heart, kidney, skeletal muscle, and liver.

Table 1 shows the results of in situ hybridization of the 3md3 probe to normal and cancer tissue samples. Each result represents the data from six separate arrays. 3md3 is expressed at a higher level in the following types of cancer compared to the corresponding normal tissue: adrenal, lung, pancreas, and thyroid. 3md3 is expressed at a lower level in the following types of cancer compared to the corresponding normal tissue: colon, esophagus, liver, prostate, and stomach. No expression was seen in samples from normal or cancerous breast, lymph node, and uterine tissue. In addition, 100% (3/3 samples, Table 2) of melanoma samples expressed 3md3, suggesting its use as a marker and a potential therapeutic target in this type of cancer.

TABLE 1

In situ Expression of 3md3 in Normal and Cancer Tissue

| Tissue Source | % expression in normal tissue | % expression in cancer tissue |
|---|---|---|
| Adrenal | 0 | 33 |
| Breast | 0 | 0 |
| Colon | 24 | 8 |
| Esophagus | 50 | 43 |
| Kidney | 71 | 29 |
| Liver | 64 | 15 |
| Lung | 5 | 10 |
| Lymph Node/Lymphoma | 0 | 0 |
| Pancreas | 55 | 75 |
| Prostate | 8 | 0 |
| Stomach | 25 | 6 |
| Thyroid | 0 | 33 |
| Uterus | 0 | 0 |

TABLE 2

In situ Expression of 3md3 in Cancer Tissue

| Cancer: Tissue Source | % expression 3md3 |
|---|---|
| Basal Cell | 0 |
| Cervical | 33 |
| Chorio | 33 |
| Epithelial | 0 |
| Fibro | 0 |
| Germ Cell | 0 |
| Leiomyo | 0 |
| Melanoma | 100 |
| Seminoma | 33 |

B. 2hd1

The second ligand is a protein encoded by SEQ ID NO:3. The sequences are shown in FIG. 6, and the ligand is referred to as 2hd1.

Example 2

Effect of Antisense Oligonucleotides on Endothelial Cell Invasion

Adrenal cortex-derived bovine microvascular endothelial (BME) cells are grown in an α-modified minimal essential medium (Life Technologies, Inc. AG, Basel, Switzerland), supplemented with 15% heat-inactivated donor calf serum (DCS, Life Technologies, Inc.), penicillin (110 units/ml), and streptomycin (110 μg/ml). BME cells are subcultured at a 1:4 split ratio in 1.5% gelatin-coated tissue culture dishes or flasks (Falcon Labware, Becton Dickinson Company, Lincoln Park, N.J.). The in vitro angiogenesis assay is performed as described (Montesano, R. et al., *Cell* 42:469–477, 1985) in 16-mm tissue culture wells (Nunclon, A/S Nunc, Roskilde, Denmark). BME cells are seeded at $5.0-7.5 \times 10^4$ cells/well in 500 μl of α-modified minimal essential medium, 5% DCS (donor calf serum). Prior to reaching confluence (less than 3 days), DCS is further reduced to 2%, and cells are treated with recombinant human FGF-2, recombinant human VEGF, and antisense oligonucleotides. Oligonucleotides are added to the cells 2 h before cytokines on the first day of treatment. Medium and cytokines are renewed after 2 days, and oligonucleotides are added either every day or every other day during the 4-day assay period. Cultures are fixed in situ after a further 2 days with 2.5% glutaraldehyde in 100 mM sodium cacodylate buffer (pH 7.4), and photographed. For quantitation, randomly selected fields measuring 1.0×1.4 mm are photographed in each well at a single level beneath the surface monolayer by phase contrast microscopy, using a Nikon Diaphot TMD inverted photomicroscope. In each experiment, invasion is quantitated from at least three photographic fields by determining the total additive length of all cellular structures that penetrate beneath the surface monolayer either as apparently single cells or in the form of cell cords or tubes. (Pepper, M. S. et al., *Biochem. Biophys. Res. Commun.* 189:824–831, 1992.)

Example 3

Expression of 3md3 in Human Microvascular Endothelial Cells

The expression of 3md3 in human microvascular endothelial cells (HMEC) is measured by assaying the mRNA in cells after a variety of treatments. mRNA expression levels are assayed by preparing probes for Northern blots as described above. bFGF-treated HMEC are prepared by incubation with bFGF at 10 mg/ml for 2 hours. VEGF-treated HMEC are prepared by incubation with 20 ng/ml VEGF for 2 hours. Following incubation with the respective growth factor, the cells are washed and lysis buffer added for RNA preparation.

The HMEC treated as above can also be exposed to one or more antisense oligomers based on SEQ ID NO: I or 3, using methods described by Zimrin, A. et al., *J. Biol. Chem.* 271:32499–32502, 1996.

Example 4

Effect of 3md3 Expression on Tumor Induced Angiogenesis In Vivo

The effect of 3md3 on tumor growth and tumor induced angiogenesis is assessed by:

(a) Infecting the highly metastatic human breast cancer cell line MDA-MB-231 with retroviruses encoding (i) the extracellular domain of 3md3, and (ii) full length 3md3. The infected cells are subsequently implanted in nude mice and the growth of the tumors as compared to control groups is monitored over time, and (b) First establishing a tumor mass by implanting MDA-MB-231 into nude mice. Adenoviruses encoding (i) the extracellular domain of 3md3, and (ii) full length 3md3 are then injected intratumorally and peritumorally. The growth of the tumors as compared to control groups is monitored over time.

Example 5

Effect of 3md3 on VEGF and bFGF Induced Angiogenesis In Vivo

Adenoviruses encoding (i) the extracellular domain of 3md3, and (ii) full length 3md3 are injected into the retroperitoneal adipose tissue alone or in combination with adenoviruses encoding VEGF or bFGF using methods described by Magovern, C. J. et al., *Hum. Gene Ther.* 8:215, 1997, and U.S. Pat. No. 5,869,037. Neovascularization of the adipose tissue is assessed on day 20 and day 30 post-injection by histological evaluation.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. An isolated nucleic acid molecule comprising a polynucleotide selected from the group consisting of:
   (a) a polynucleotide encoding amino acids from about 1 to about 583 of SEQ ID NO:2;
   (b) a polynucleotide encoding amino acids from about 2 to about 583 of SEQ ID NO:2;
   (c) the polynucleotide complement of the polynucleotide of (a) or (b); and
   (d) a polynucleotide at least 90% identical to the polynucleotide of (a)–(c), wherein the polynucleotide encodes a polypeptide that promotes angiogenesis.

2. The isolated nucleic acid molecule of claim 1, which is DNA.

3. A method of making a recombinant vector comprising inserting a nucleic acid molecule of claim 1 into a vector in operable linkage to a promoter.

4. A recombinant vector produced by the method of claim 3.

5. A method of making a recombinant host cell comprising introducing the recombinant vector of claim 4 into a host.

6. A recombinant host cell produced by the method on claim 5.

7. A recombinant method of producing a polypeptide of claim 1, comprising culturing a recombinant host cell comprising a nucleic acid molecule encoding said polypeptide under conditions such that said polypeptide is expressed and recovering said polypeptide.

8. An isolated nucleic acid molecule consisting of a nucleic acid comprising 500–1000 contiguous nucleotides from the coding region of SEQ ID NO:1.

9. An isolated nucleic acid molecule comprising a polynucleotide encoding a polypeptide at least 90% identical to a polypeptide selected from the group consisting of:
   (a) amino acids from about 1 to about 583 of SEQ ID NO:2; and
   (b) amino acids from about 2 to about 583 of SEQ ID NO:2, wherein the polypeptide promotes angiogenesis.

* * * * *

SEQUENCE LISTING

<160> NUMBER OF SEQ ID NOS: 10

<210> SEQ ID NO 1
<211> LENGTH: 1752
<212> TYPE: DNA
<213> ORGANISM: Homo sapiens

<400> SEQUENCE: 1

```
atggtctccc cacggatgtc cgggctcctc tcccagactg tgatcctagc gctcattttc      60
ctcccccaga cacggcccgc tggcgtcttc gagctgcaga tccactcttt cgggccgggt     120
ccaggccctg gggccccgcg gtcccctgc agcgcccggc tccctgccg cctcttcttc      180
```

-continued

```
agagtctgcc tgaagcctgg gctctcagag gaggccgccg agtccccgtg cgccctgggc    240
gcggcgctga gtgcgcgcgg accggtctac accgagcagc ccggagcgcc cgcgcctgat    300
ctcccactgc ccgacggcct cttgcaggtg cccttccggg acgcctggcc tggcaccttc    360
tctttcatca tcgaaacctg gagagaggag ttaggagacc agattggagg gcccgcctgg    420
agcctgctgg cgcgcgtggc tggcaggcgg cgcttggcag ccggaggccc gtgggcccgg    480
gacattcagc gcgcaggcgc ctgggagctg cgctgctcgt accgcgcgcg ctgcgagccg    540
cctgcggtcg ggaccgcgtg cacgcgcctc tgccgtccgc gcagcgcccc ctcgcggtgc    600
ggtccgggac tgcgcccctg cgcaccgctc gaggacgaat cggtgtgccg agcaggctgc    660
agccctgagc atggcttctg tgaacagccc ggtgaatgcc gatgcctaga gggctggact    720 ggaccccctct gcacggtccc tgtctccacc agcagctgcc tcagcccag gggcccgtcc    780 tctgctacca ccgatgcct tgtccctggg cctgggccct gtgacgggaa cccgtgtgcc    840
aatggaggca gctgtagtga cacccagg tcctttgaat gcacctgccc gcgtgggttc    900
tacgggctgc ggtgtgaggt gagcggggtg acatgtgcag atggaccctg cttcaacggc    960
ggcttgtgtg tcgggggtgc agaccctgac tctgcctaca tctgccactg cccacctggt   1020
ttccaaggct ccaactgtga agagggtg gaccggtgca gcctgcagcc atgccgcaat   1080 gcggactct gcctggacct gggccacgcc ctgcgctgcc gctgccgcgc cggcttcgcg   1140
ggtcctcgct gcgagcacga cctggacgac tgcgcgggcc gcgcctgcgc taacggcggc   1200
acgtgtgtgg agggcggcgg cgcgcaccgc tgctcctgcg cgctgggctt cggcggccgc   1260
gactgccgcg agcgcgcgga cccgtgcgcc gcgcgcccct gtgctcacgg cggccgctgc   1320
tacgcccact tctccggcct cgtctgcgct tgcgctcccg gctacatggg agcgcggtgt   1380
gagttcccag tgcaccccga cggcgcaagc gccttgcccg cggccccgcc gggcctcagg   1440
cccggggacc ctcagcgcta ccttttgcct ccggctctgg gactgctcgt ggccgcgggc   1500
gtggccggcg ctgcgctctt gctggtccac gtgcgccgcc gtggccactc ccaggatgct   1560
gggtctcgct tgctggctgg accccggag ccgtcagtcc acgcactccc ggatgcactc   1620
aacaacctaa ggacgcagga gggttccggg gatggtccga gctcgtccgt agattggaat   1680
cgccctgaag atgtagaccc tcaagggatt tatgtcatat ctgctccttc catctacgct   1740
cgggaggcct ga                                                      1752
```

<210> SEQ ID NO 2
<211> LENGTH: 583
<212> TYPE: PRT
<213> ORGANISM: Homo sapiens

<400> SEQUENCE: 2

```
Met Val Ser Pro Arg Met Ser Gly Leu Leu Ser Gln Thr Val Ile Leu
  1               5                  10                  15

Ala Leu Ile Phe Leu Pro Gln Thr Arg Pro Ala Gly Val Phe Glu Leu
             20                  25                  30

Gln Ile His Ser Phe Gly Pro Gly Pro Gly Pro Gly Ala Pro Arg Ser
         35                  40                  45

Pro Cys Ser Ala Arg Leu Pro Cys Arg Leu Phe Phe Arg Val Cys Leu
     50                  55                  60

Lys Pro Gly Leu Ser Glu Glu Ala Ala Glu Ser Pro Cys Ala Leu Gly
 65                  70                  75                  80

Ala Ala Leu Ser Ala Arg Gly Pro Val Tyr Thr Glu Gln Pro Gly Ala
```

```
                    85                  90                      95
Pro Ala Pro Asp Leu Pro Leu Pro Asp Gly Leu Leu Gln Val Pro Phe
            100             105                 110
Arg Asp Ala Trp Pro Gly Thr Phe Ser Phe Ile Ile Glu Thr Trp Arg
            115             120                 125
Glu Glu Leu Gly Asp Gln Ile Gly Gly Pro Ala Trp Ser Leu Leu Ala
    130                 135                 140
Arg Val Ala Gly Arg Arg Leu Ala Ala Gly Gly Pro Trp Ala Arg
145                 150                 155                 160
Asp Ile Gln Arg Ala Gly Ala Trp Glu Leu Arg Cys Ser Tyr Arg Ala
                165                 170                 175
Arg Cys Glu Pro Pro Ala Val Gly Thr Ala Cys Thr Arg Leu Cys Arg
            180                 185                 190
Pro Arg Ser Ala Pro Ser Arg Cys Gly Pro Gly Leu Arg Pro Cys Ala
            195                 200                 205
Pro Leu Glu Asp Glu Ser Val Cys Arg Ala Gly Cys Ser Pro Glu His
        210                 215                 220
Gly Phe Cys Glu Gln Pro Gly Glu Cys Arg Cys Leu Glu Gly Trp Thr
225                 230                 235                 240
Gly Pro Leu Cys Thr Val Pro Val Ser Thr Ser Ser Cys Leu Ser Pro
                245                 250                 255
Arg Gly Pro Ser Ser Ala Thr Thr Gly Cys Leu Val Pro Gly Pro Gly
            260                 265                 270
Pro Cys Asp Gly Asn Pro Cys Ala Asn Gly Gly Ser Cys Ser Glu Thr
            275                 280                 285
Pro Arg Ser Phe Glu Cys Thr Cys Pro Arg Gly Phe Tyr Gly Leu Arg
        290                 295                 300
Cys Glu Val Ser Gly Val Thr Cys Ala Asp Gly Pro Cys Phe Asn Gly
305                 310                 315                 320
Gly Leu Cys Val Gly Gly Ala Asp Pro Asp Ser Ala Tyr Ile Cys His
                325                 330                 335
Cys Pro Pro Gly Phe Gln Gly Ser Asn Cys Glu Lys Arg Val Asp Arg
            340                 345                 350
Cys Ser Leu Gln Pro Cys Arg Asn Gly Gly Leu Cys Leu Asp Leu Gly
            355                 360                 365
His Ala Leu Arg Cys Arg Cys Arg Ala Gly Phe Ala Gly Pro Arg Cys
        370                 375                 380
Glu His Asp Leu Asp Asp Cys Ala Gly Arg Ala Cys Ala Asn Gly Gly
385                 390                 395                 400
Thr Cys Val Glu Gly Gly Ala His Arg Cys Ser Cys Ala Leu Gly
                405                 410                 415
Phe Gly Gly Arg Asp Cys Arg Glu Arg Ala Asp Pro Cys Ala Ala Arg
            420                 425                 430
Pro Cys Ala His Gly Gly Arg Cys Tyr Ala His Phe Ser Gly Leu Val
            435                 440                 445
Cys Ala Cys Ala Pro Gly Tyr Met Gly Ala Arg Cys Glu Phe Pro Val
        450                 455                 460
His Pro Asp Gly Ala Ser Ala Leu Pro Ala Ala Pro Gly Leu Arg
465                 470                 475                 480
Pro Gly Asp Pro Gln Arg Tyr Leu Leu Pro Ala Leu Gly Leu Leu
                485                 490                 495
Val Ala Ala Gly Val Ala Gly Ala Ala Leu Leu Leu Val His Val Arg
            500                 505                 510
```

-continued

```
Arg Arg Gly His Ser Gln Asp Ala Gly Ser Arg Leu Leu Ala Gly Thr
    515                 520                 525

Pro Glu Pro Ser Val His Ala Leu Pro Asp Ala Leu Asn Asn Leu Arg
    530                 535                 540

Thr Gln Glu Gly Ser Gly Asp Gly Pro Ser Ser Ser Val Asp Trp Asn
545                 550                 555                 560

Arg Pro Glu Asp Val Asp Pro Gln Gly Ile Tyr Val Ile Ser Ala Pro
                565                 570                 575

Ser Ile Tyr Ala Arg Glu Ala
            580
```

```
<210> SEQ ID NO 3
<211> LENGTH: 1307
<212> TYPE: DNA
<213> ORGANISM: Homo sapiens

<400> SEQUENCE: 3
agtactccta ccgcttcgtg tgtgacgaac actactacgg agagggctgc tccgttttct    60
gccgtccccg ggacgatgcc ttcggccact tcacctgtgg ggagcgtggg gagaaagtgt   120
gcaaccctgg ctggaaaggg ccctactgca cagagcgtga gtctctggga aggcaccgct   180
ggctcactcg tccacgaaca cggaccacgc gcagggacgg gcttcctga gccacggggg    240
gcttgggact gtagagatgt tctggtgggg aaactgaggc ccagaggaca gaagtggatt   300
gctataagtc acagctcgtc agtgggggg ttggggtcaa cgcagacatt ttaacatccc    360
aggctgtgtt tatccactat cggaactgcc tttcttaatc agggaggatt ttagagacag   420
ggccaggggt caggaagtaa agccagtgct accccaggt tgtgtgtatt agagagggag    480
aggaggaagg aagggaggaa cacagagaga gcttgtgtgt cagggcacc atttcaaccc    540
gagttcccag tgctggaaca gcatcacact gggaaacgtt ccattttctc tctggagctg   600
gtgtgcttga cctctctgga gcaaacgcct ttccggatac tccctgtgac acgcactgtc   660
tatgctggcc agagagcagg ctttcactcc tgtgggctgc tgaggccagg tctccaaggc   720
ctgtgtgggc gaggggtgca cagccccgtc tggcttgaat gctcaggcag caccttgtct   780
ggaaaagcaa tgtcttccca atagtgacag aggctctacc tgcctcttat taggtattga   840
tgtgtcaatg tcatggcagg caggtgacta gggcagggtt ggggccgtgc tggctcctgg   900
ttctggctca tgggacctc aggagccctc tctccagctg actgaggcct cgcctgcacg    960
cctggccgtc ccagcccatt ggtaccggat ttctctacag ctggggattg gtaggtcct   1020
ggagctgccc agaaactcca gggaactgtc attctccttc cttggaactg acaaccttg   1080
gagagggct ctgggaggcc cagaacctct ggcaggagct gggtagtgcc tggggttgag   1140
ggtgggtctt cccattcact gagtgccttg atgtccttgc tccttagctt cccaaattcc  1200
ctccggaact tactgagctc cttctaagct ttgccttggc ctgaactggt tctggggaaa  1260
aaaaaaaaaa aaaaaaaaa aaaaaaaaa aaaaaaaaa aaaaaaa                  1307
```

```
<210> SEQ ID NO 4
<211> LENGTH: 81
<212> TYPE: PRT
<213> ORGANISM: Homo sapiens

<400> SEQUENCE: 4

Gly Arg Thr Asp Leu Lys Tyr Ser Tyr Arg Phe Val Cys Asp Glu His
  1               5                  10                  15
```

-continued

```
Tyr Tyr Gly Glu Gly Cys Ser Val Phe Cys Arg Pro Arg Asp Asp Ala
             20                  25                  30

Phe Gly His Phe Thr Cys Gly Glu Arg Gly Glu Lys Val Cys Asn Pro
             35                  40                  45

Gly Trp Lys Gly Pro Tyr Cys Thr Glu Arg Glu Ser Leu Gly Arg His
 50                  55                  60

Arg Trp Leu Thr Arg Pro Arg Thr Arg Thr Thr Arg Arg Asp Gly Ala
 65                  70                  75                  80

Ser

<210> SEQ ID NO 5
<211> LENGTH: 585
<212> TYPE: PRT
<213> ORGANISM: Mus musculus
<220> FEATURE:
<221> NAME/KEY: VARIANT
<222> LOCATION: (1)...(585)
<223> OTHER INFORMATION: Xaa = Any Amino Acid

<400> SEQUENCE: 5

Met Val Ser Leu Gln Val Ser Pro Leu Ser Gln Thr Leu Ile Leu Ala
 1               5                  10                  15

Phe Leu Leu Pro Gln Ala Leu Pro Ala Gly Val Phe Glu Leu Gln Ile
             20                  25                  30

His Ser Phe Gly Pro Gly Pro Gly Leu Gly Thr Pro Arg Ser Pro Cys
             35                  40                  45

Asn Ala Arg Gly Pro Cys Arg Leu Phe Phe Arg Val Cys Leu Lys Pro
 50                  55                  60

Gly Val Ser Gln Glu Ala Thr Glu Ser Leu Cys Ala Leu Gly Ala Ala
 65                  70                  75                  80

Leu Ser Thr Ser Val Pro Val Tyr Thr Glu His Pro Gly Glu Ser Ala
             85                  90                  95

Ala Ala Leu Pro Leu Pro Asp Gly Leu Val Arg Val Pro Phe Arg Asp
            100                 105                 110

Ala Trp Pro Gly Thr Phe Ser Leu Val Ile Glu Thr Trp Arg Glu Gln
            115                 120                 125

Leu Gly Glu His Ala Gly Gly Pro Ala Trp Asn Leu Leu Ala Arg Val
130                 135                 140

Val Gly Arg Arg Arg Leu Ala Ala Gly Gly Pro Trp Ala Arg Asp Val
145                 150                 155                 160

Gln Arg Thr Gly Thr Trp Glu Leu His Phe Ser Tyr Arg Ala Arg Cys
                165                 170                 175

Glu Pro Pro Ala Val Gly Ala Ala Cys Ala Arg Leu Cys Arg Ser Arg
            180                 185                 190

Ser Ala Pro Ser Arg Cys Gly Pro Gly Leu Arg Pro Cys Thr Pro Phe
            195                 200                 205

Pro Asp Glu Cys Glu Ala Pro Ser Val Cys Arg Pro Gly Cys Ser Pro
210                 215                 220

Glu His Gly Tyr Cys Glu Pro Asp Glu Cys Arg Cys Leu Glu Gly
225                 230                 235                 240

Trp Thr Gly Pro Leu Cys Thr Val Pro Val Ser Thr Ser Ser Cys Leu
                245                 250                 255

Asn Ser Arg Val Pro Gly Pro Ala Ser Thr Gly Cys Leu Leu Pro Gly
            260                 265                 270

Pro Gly Pro Cys Asp Gly Asn Pro Cys Ala Asn Gly Gly Ser Cys Ser
            275                 280                 285
```

```
Glu Thr Ser Gly Ser Phe Glu Cys Ala Cys Pro Arg Gly Phe Tyr Gly
    290                 295                 300

Leu Arg Cys Glu Val Ser Gly Val Thr Cys Ala Asp Gly Pro Cys Phe
305                 310                 315                 320

Asn Gly Gly Leu Cys Val Gly Gly Glu Asp Pro Asp Ser Xaa Tyr Val
                325                 330                 335

Cys His Cys Pro Pro Gly Phe Gln Gly Ser Asn Cys Glu Lys Arg Val
                340                 345                 350

Asp Arg Cys Ser Leu Gln Pro Cys Gln Asn Gly Gly Leu Cys Leu Asp
            355                 360                 365

Leu Gly His Ala Xaa Xaa Cys Arg Cys Arg Ala Gly Phe Ala Gly Pro
    370                 375                 380

Arg Cys Glu His Asp Leu Asp Asp Cys Ala Gly Arg Ala Cys Ala Asn
385                 390                 395                 400

Ala Gly Thr Cys Val Glu Gly Gly Ser Arg Arg Cys Ser Cys Ala
                405                 410                 415

Leu Gly Phe Gly Gly Arg Asp Cys Arg Glu Arg Ala Asp Pro Cys Ala
                420                 425                 430

Ser Arg Pro Cys Ala His Gly Gly Arg Cys Tyr Ala His Phe Ser Gly
            435                 440                 445

Leu Val Cys Ala Cys Ala Pro Gly Tyr Met Gly Val Arg Cys Glu Phe
    450                 455                 460

Ala Val Arg Pro Asp Gly Ala Asp Ala Val Pro Ala Pro Arg Gly
465                 470                 475                 480

Leu Arg Gln Ala Asp Pro Gln Arg Phe Leu Leu Pro Pro Ala Leu Gly
                485                 490                 495

Leu Leu Val Ala Ala Gly Leu Ala Gly Ala Ala Leu Leu Val Ile His
                500                 505                 510

Val Arg Arg Arg Gly Pro Gly Gln Asp Thr Gly Thr Arg Leu Leu Ser
            515                 520                 525

Gly Thr Arg Glu Pro Ser Val His Thr Leu Pro Asp Ala Leu Asn Asn
530                 535                 540

Leu Arg Leu Gln Asp Gly Ala Gly Asp Gly Pro Ser Ser Ser Ala Asp
545                 550                 555                 560

Trp Asn His Pro Glu Asp Gly Asp Ser Arg Ser Ile Tyr Val Ile Pro
                565                 570                 575

Ala Pro Ser Ile Tyr Ala Arg Glu Ala
                580                 585

<210> SEQ ID NO 6
<211> LENGTH: 723
<212> TYPE: PRT
<213> ORGANISM: Homo sapiens

<400> SEQUENCE: 6

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Pro Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
```

-continued

```
            65                  70                  75                  80
Ser Ala Val Thr Pro Val Leu Gly Val Asp Ser Phe Ser Leu Pro Asp
                    85                  90                  95
Gly Gly Gly Ala Asp Ser Ala Phe Ser Asn Pro Ile Arg Phe Pro Phe
                100                 105                 110
Gly Phe Thr Trp Pro Gly Thr Phe Ser Leu Ile Ile Glu Ala Leu His
                115                 120                 125
Thr Asp Ser Pro Asp Asp Leu Ala Thr Glu Asn Pro Glu Arg Leu Ile
            130                 135                 140
Ser Pro Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
                180                 185                 190
Arg Pro Arg Asp Asp Ala Phe Gly His Phe Thr Cys Gly Glu Arg Gly
                195                 200                 205
Glu Lys Val Cys Asn Pro Gly Trp Lys Gly Pro Tyr Cys Thr Glu Pro
            210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
                245                 250                 255
Cys Ile Arg Tyr Pro Gly Cys Leu His Gly Thr Cys Gln Gln Pro Trp
                260                 265                 270
Gln Cys Asn Cys Gln Glu Gly Trp Gly Gly Leu Phe Cys Asn Gln Asp
            275                 280                 285
Leu Asn Tyr Cys Thr His His Lys Pro Cys Lys Asn Gly Ala Thr Cys
            290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
                340                 345                 350
Thr Cys Pro Pro Gly Phe Tyr Gly Lys Ile Cys Glu Leu Ser Ala Met
                355                 360                 365
Thr Cys Ala Asp Gly Pro Cys Phe Asn Gly Gly Arg Cys Ser Asp Ser
            370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Ser Pro Cys Ser Asn
                405                 410                 415
Gly Ala Lys Cys Val Asp Leu Gly Asp Ala Tyr Leu Cys Arg Cys Gln
                420                 425                 430
Ala Gly Phe Ser Gly Arg His Cys Asp Asp Asn Val Asp Asp Cys Ala
                435                 440                 445
Ser Ser Pro Cys Ala Asn Gly Gly Thr Cys Arg Asp Gly Val Asn Asp
            450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
```

```
His Glu Arg Gly His Gly Tyr Val Cys Glu Cys Ala Arg Gly Tyr Gly
                500                 505                 510

Gly Pro Asn Cys Gln Phe Leu Leu Pro Glu Leu Pro Pro Gly Pro Ala
            515                 520                 525

Val Val Asp Leu Thr Glu Lys Leu Glu Gly Gln Gly Gly Pro Phe Pro
        530                 535                 540

Trp Val Ala Val Cys Ala Gly Val Ile Leu Val Leu Met Leu Leu Leu
545                 550                 555                 560

Gly Cys Ala Ala Val Val Val Cys Val Pro Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
        610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
        690                 695                 700

Gln Ser Val Tyr Val Ile Ser Glu Glu Lys Asp Glu Cys Val Ile Ala
705                 710                 715                 720

Thr Glu Val

<210> SEQ ID NO 7
<211> LENGTH: 685
<212> TYPE: PRT
<213> ORGANISM: Homo sapiens

<400> SEQUENCE: 7

Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
 65                 70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140
```

-continued

```
Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560
```

-continued

```
Asp Asp Gly Ser Arg Glu Ala Met Asn Asn Leu Ser Asp Phe Gln Lys
            565                 570                 575

Asp Asn Leu Ile Pro Ala Ala Gln Leu Lys Asn Thr Asn Gln Lys Lys
        580                 585                 590

Glu Leu Glu Val Asp Cys Gly Leu Asp Lys Ser Asn Cys Gly Lys Gln
    595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
            645                 650                 655

Ala Met Cys Ser Pro Arg Asp Ser Met Tyr Gln Ser Val Cys Leu Ile
        660                 665                 670

Ser Glu Glu Arg Asn Glu Cys Val Ile Ala Thr Glu Val
    675                 680                 685
```

<210> SEQ ID NO 8
<211> LENGTH: 1758
<212> TYPE: DNA
<213> ORGANISM: Mus musculus
<220> FEATURE:
<221> NAME/KEY: misc_feature
<222> LOCATION: (1)...(1758)
<223> OTHER INFORMATION: n = A,T,C or G

<400> SEQUENCE: 8

```
atggtctctc tgcaggtgtc tccgctttcc cagacgctga tcctggcttt tcttcttcct      60
caggcactgc cagctggtgt cttcgagcta caaattcatt ctttcgggcc aggcccaggc     120
ctcgggaccc cacgctcccc ctgcaacgcc cgaggccctt gccgcctctt cttcagggtc     180
tgcctgaagc ccggagtctc ccaggaggcc accgagtccc tgtgcgccct gggngcagca     240
ctgagcacga gcgtcccggt ctatacggag caccccggag agtcagcggc tgccctgccg     300
ctgcctgatg gcctcgtacg tgtgcccttc gcgatgctt ggccgggcac cttctccctc     360
gtcattgaaa cctggagaga gcagctggga gagcatgctg agggcccgc ctggaacctg     420
ctagcacgtg tggtcggccg tagacgcctg gcggctgggg gcccgtgggc ccgcgatgtg     480
cagcgcacag gcacatggga gttgcacttc tcctaccgcg cgcggtgcga gccgcccgcc     540
gtcgggggcg cctgcgcgcg cctgtgccgc tcacgcagtg cccctcgcg gtgtggcccg     600
ggactgcgac cctgcacgcc attcccagac gagtgcgaag cccgtctgt gtgtcgacca     660
ggctgcagcc ccgagcacgg ctactgtgaa gagcctgatg aatgccgttg cctggagggc     720
tggactggac ccctctgcac ggtccctgtc tccaccagta gctgcctgaa ctccagggtt     780
cctggtcctg ccagcactgg atgccttttta cctgggcctg gaccttgtga tgggaaccca     840
tgtgccaatg ggggcagctg tagtgaaacc tctggctcct ttgaatgtgc ctgtccccgg     900
ggattctacg gcttcgatg tgaggtgagc ggggtcacgt gcgcagatgg acctgcttc      960
aatgcgggct tgtgtgttgg cggtgaagat cctgactctn cctatgtctg tcattgccca    1020
cctggtttcc aaggctctaa ctgtgagaag agggtggacc gctgtagcct gcagccatgt    1080
cagaatggcg gcctctgcct ggacctgggc cacgcgttnn cctgccgctg tcgcgcggga    1140
ttcgccgggc cgcgctgcga gcacgacctg gacgactgcg ccggccgcgc ctgtgccaac    1200
gcgggcacgt gcgttgaggg cggcggctcg cgccgctgct cctgtgcgct gggcttcggc    1260
gggcgcgact gccgagaacg cgcggaccct tgcgcctccc gccctgcgc gcatggaggc    1320
```

-continued

| | |
|---|---|
| cgttgctacg cccacttctc tggcctggtc tgcgcctgcg cgcccggcta catgggcgtg | 1380 |
| agatgcgagt tcgctgtgcg cccggacggc gcggacgcgg tgcccgccgc cccgcggggc | 1440 |
| ctgaggcagg cggatccaca gcgctttctt ctgcctcccg ccttggggct gctggtggcc | 1500 |
| gccggtttgg ctggcgccgc actcttggtc atccacgttc gccgccgagg tcctggccag | 1560 |
| gataccggga ctcgcctgct ttctgggacc cgggagcctt cggtccacac gctcccggat | 1620 |
| gcactcaaca acctgaggtt acaagacggt gctgggatg gccccagttc gtcggctgac | 1680 |
| tggaatcatc ctgaagatgg agactctaga tccatttatg tcataccagc cccttccatt | 1740 |
| tatgcacgag aggcctga | 1758 |

<210> SEQ ID NO 9
<211> LENGTH: 2183
<212> TYPE: DNA
<213> ORGANISM: Homo sapiens

<400> SEQUENCE: 9

| | |
|---|---|
| atgggcagtc ggtgcgcgct ggccctggcg gtgctctcgg ccttgctgtg tcaggtctgg | 60 |
| agctctgggg tgttcgaact gaagctgcag gagttcgtca acaagaaggg gctgctgggg | 120 |
| aaccgcaact gctgccgcgg gggcgcgggg ccaccgccgt gcgcctgccg gaccttcttc | 180 |
| cgcgtgtgcc tcaagcacta ccaggccagc gtgtcccccg agccgccctg cacctacggc | 240 |
| agcgccgtca cccccgtgct gggcgtcgac tccttcagtc tgcccgacgg cggggggcgcc | 300 |
| gactccgcgt tcagcaaccc catccgcttc cccttcggct tcacctggcc gggcaccttc | 360 |
| tctctgatta ttgaagctct ccacacagat tctcctgatg acctcgcaac agaaaaccca | 420 |
| gaaagactca tcagccgcct ggccacccag aggcacctga cggtgggcga ggagtggtcc | 480 |
| caggacctgc acagcagcgg ccgcacggac ctcaagtact cctaccgctt cgtgtgtgac | 540 |
| gaacactact acggagaggg ctgctccgtt ttctgccgtc cccgggacga tgccttcggc | 600 |
| cacttcacct gtggggagcg tggggagaaa gtgtgcaacc ctggctggaa agggccctac | 660 |
| tgcacagagc cgatctgcct gcctggatgt gatgagcagc atggattttg tgacaaacca | 720 |
| ggggaatgca gtgcagagt gggctggcag ggccggtact gtgacgagtg tatccgctat | 780 |
| ccaggctgtc tccatggcac ctgccagcag ccctggcagt gcaactgcca ggaaggctgg | 840 |
| gggggccttt tctgcaacca ggacctgaac tactgcacac accataagcc ctgcaagaat | 900 |
| ggagccacct gcaccaacac gggccagggg agctacactt gctcttgccg gcctgggtac | 960 |
| acaggtgcca cctgcgagct ggggattgac gagtgtgacc cagcccttg taagaacgga | 1020 |
| gggagctgca cggatctcga aacagctac tcctgtacct gccacccgg cttctacggc | 1080 |
| aaaatctgtg aattgagtgc catgacctgt gcggacggcc cttgctttaa cggggtcgg | 1140 |
| tgctcagaca gccccgatgg agggtacagc tgccgctgcc ccgtgggcta ctccggcttc | 1200 |
| aactgtgaga agaaaattga ctactgcagc tcttcaccct gttctaatgg tgccaagtgt | 1260 |
| gtggacctcg gtgatgccta cctgtgccgc tgccaggccg gcttctcggg gaggcactgt | 1320 |
| gacgacaacg tggacgactg cgcctcctcc ccgtgcgcca acggggcac ctgccgggat | 1380 |
| ggcgtgaacc acttctcctg cacctgcccg cctggctaca cgggcaggaa ctgcagtgcc | 1440 |
| cccgtcagca ggtgcgagca cgcccctgc acaatggggg ccacctgcca cgagagggc | 1500 |
| cacggctatg tgtgcgagtg tgcccgaggc tacgggggtc ccaactgcca gttcctgctc | 1560 |
| cccgagctgc ccccgggccc agcggtggtg gacctcactg agaagctaga gggccaggc | 1620 |

-continued

| | |
|---|---|
| gggccattcc cctgggtggc cgtgtgcgcc ggggtcatcc ttgtcctcat gctgctgctg | 1680 |
| ggctgtgccg ctgtggtggt ctgcgtccgg ctgaggctgc agaagcaccg gcccccagcc | 1740 |
| gacccctgcc gggggagac ggagaccatg aacaacctgg ccaactgcca gcgtgagaag | 1800 |
| gacatctcag tcagcatcat cggggccacg cagatcaaga acaccaacaa gaaggcggac | 1860 |
| ttccacgggg accacagcgc cgacaagaat ggcttcaagg cccgctaccc agcggtggac | 1920 |
| tataacctcg tgcaggacct caagggtgac gacaccgccg tcagggacgc gcacagcaag | 1980 |
| cgtgacacca agtgccagcc ccagggctcc tcaggggagg agaagggggac cccgaccaca | 2040 |
| ctcaggggtg gagaagcatc tgaaagaaaa aggccggact cgggctgttc aacttcaaaa | 2100 |
| gacaccaagt accagtcggt gtacgtcata tccgaggaga aggatgagtg cgtcatagca | 2160 |
| actgaggtgt aaaatggaag tga | 2183 |

<210> SEQ ID NO 10
<211> LENGTH: 2055
<212> TYPE: DNA
<213> ORGANISM: Homo sapiens

<400> SEQUENCE: 10

| | |
|---|---|
| atggcggcag cgtcccggag cgcctctggc tgggcgctac tgctgctggt ggcactttgg | 60 |
| cagcagcgcg cggccggctc cggcgtcttc cagctgcagc tgcaggagtt catcaacgag | 120 |
| cgcggcgtac tggccagtgg gcggccttgc gagcccggct gccggacttt cttccgcgtc | 180 |
| tgccttaagc acttccaggc ggtcgtctcg cccggaccct gcaccttcgg gaccgtctcc | 240 |
| acgccggtat tgggcaccaa ctccttcgct gtccgggacg acagtagcgg cggggggcgc | 300 |
| aaccctctcc aactgcccct caatttcacc tggccgggta ccttctcgct catcatcgaa | 360 |
| gcttggcacg cgccaggaga cgacctgcgg ccagaggcct gccaccaga tgcactcatc | 420 |
| agcaagatcg ccatccaggg ctccctagct gtgggtcaga actggttatt ggatgagcaa | 480 |
| accagcaccc tcacaaggct gcgctactct taccgggtca tctgcagtga caactactat | 540 |
| ggagacaact gctcccgcct gtgcaagaag cgcaatgacc acttcggcca ctatgtgtgc | 600 |
| cagccagatg gcaacttgtc ctgcctgccc ggttggactg gggaatattg ccaacagcct | 660 |
| atctgtcttt cggctgtca tgaacagaat ggctactgca gcaagccagc agagtgcctc | 720 |
| tgccgcccag gctggcaggg ccggctgtgt aacgaatgca tcccccacaa tggctgtcgc | 780 |
| cacggcacct gcagcactcc ctggcaatgt acttgtgatg agggctgggg aggcctgttt | 840 |
| tgtgaccaag atctcaacta ctgcacccac cactccccat gcaagaatgg gcaacgtgc | 900 |
| tccaacagtg ggcagcgaag ctacacctgc acctgtcgcc caggctacac tggtgtggac | 960 |
| tgtgagctgg agctcagcga gtgtgacagc aaccctgtc gcaatggagg cagctgtaag | 1020 |
| gaccaggagg atggctacca ctgcctgtgt cctccgggct actatggcct gcattgtgaa | 1080 |
| cacagcacct tgagctgcgc cgactccccc tgcttcaatg ggggctcctg ccgggagcgc | 1140 |
| aaccaggggg ccaactatgc ttgtgaatgt cccccaact tcaccggctc caactgcgag | 1200 |
| aagaaagtgg acaggtgcac cagcaacccc tgtgccaacg ggggacagtg cctgaaccga | 1260 |
| ggtccaagcc gcatgtgccg ctgccgtcct ggattcacgg gcacctactg tgaactccac | 1320 |
| gtcagcgact gtgcccgtaa cccttgcgcc cacggtggca cttgccatga cctggagaat | 1380 |
| gggctcatgt gcacctgccc tgccggcttc tctggccgac gctgtgaggt gcggacatcc | 1440 |
| atcgatgcct gtgcctcgag tccctgcttc aacagggcca cctgctacac cgacctctcc | 1500 |
| acagacacct ttgtgtgcaa ctgcccttat ggctttgtgg gcagccgctg cgagttcccc | 1560 |

```
gtgggcttgc cgcccagctt cccctggtg gccgtctcgc tgggtgtggg gctggcagtg    1620
ctgctggtac tgctgggcat ggtggcagtg gctgtgcggc agctgcggct tcgacggccg    1680
gacgacggca gcagggaagc catgaacaac ttgtcggact tccagaagga caacctgatt    1740
cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc gggggaccat gccaggaaag tttccccaca gtgacaagag cttaggagag    1920
aaggcgccac tgcggttaca cagtgaaaag ccagagtgtc ggatatcagc gatgtgctcc    1980
cccagggact ccatgtacca gtctgtgtgt ttgatatcag aggagaggaa tgaatgtgtc    2040
attgccacgg aggta                                                    2055
```